US012799449B2

(12) United States Patent
Kondo et al.

(10) Patent No.: US 12,799,449 B2
(45) Date of Patent: Nov. 17, 2026

(54) METALLIC POROUS MEMBRANE, CLASSIFYING METHOD USING THE SAME, AND CLASSIFYING DEVICE

(71) Applicant: Murata Manufacturing Co., Ltd., Nagaokakyo (JP)

(72) Inventors: Takashi Kondo, Nagaokakyo (JP); Masaru Banju, Nagaokakyo (JP); Junko Watanabe, Nagaokakyo (JP); Makoto Hasegawa, Nagaokakyo (JP); Tamio Mizukami, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 519 days.

(21) Appl. No.: 18/475,846

(22) Filed: Sep. 27, 2023

(65) Prior Publication Data

US 2024/0018462 A1 Jan. 18, 2024

Related U.S. Application Data

(60) Division of application No. 16/951,420, filed on Nov. 18, 2020, now abandoned, which is a continuation of (Continued)

(30) Foreign Application Priority Data

Mar. 18, 2016 (JP) ................................ 2016-055475
Sep. 5, 2016 (JP) ................................ 2016-172839

(51) Int. Cl.
*B01L 7/00* (2006.01)
*B01D 15/08* (2006.01)
(Continued)

(52) U.S. Cl.
CPC ............ *C12M 47/04* (2013.01); *B01D 39/10* (2013.01); *B01D 39/20* (2013.01);
(Continued)

(58) Field of Classification Search
CPC ........ C12M 47/04; B01D 39/10; B01D 39/20; B01D 2239/1208; G01N 15/0272; G01N 1/28; G01N 15/01; G01N 2015/0053
See application file for complete search history.

(56) References Cited

U.S. PATENT DOCUMENTS 5,427,664 A * 6/1995 Stoev ................ G01N 15/0272 204/542
9,194,865 B2 11/2015 Ito
(Continued)

FOREIGN PATENT DOCUMENTS

JP 4142441 A 5/1992
JP 2013042689 A 3/2013
(Continued)

OTHER PUBLICATIONS

International Search Report issued in International Application No. PCT/JP2017/008145, date of mailing Apr. 4, 2017.
(Continued)

*Primary Examiner* — Oyeleye Alexander Alabi
(74) *Attorney, Agent, or Firm* — ArentFox Schiff LLP

(57) ABSTRACT

A classifying device that classifies aggregates and includes: a plurality of metallic porous membranes respectively including: a membrane section including a first principal surface, a second principal surface, and a plurality of through-holes. Among each of the plurality of metallic porous membranes, the through-holes have mutually different dimensions, and some of the plurality of through-holes in at least a first of the plurality of metallic porous membranes are configured to have different dimensions sufficient to release pressure applied to the first of the plurality of metallic porous membranes without degrading classification accuracy of the first of the plurality of metallic porous membranes. The plurality of metallic porous membranes are arranged in series from an upstream side of a flow path
(Continued)

through which a liquid containing the aggregates flows in a descending order of the different dimensions of the through-holes of the plurality of metallic porous membranes.

7 Claims, 24 Drawing Sheets

Related U.S. Application Data application No. 16/114,454, filed on Aug. 28, 2018, now Pat. No. 10,889,796, which is a continuation of application No. PCT/JP2017/008145, filed on Mar. 1, 2017.

(51) Int. Cl.

| | |
|---|---|
| ***B01D 39/10*** | (2006.01) |
| ***B01D 39/20*** | (2006.01) |
| ***B01F 33/302*** | (2022.01) |
| ***B01F 33/3033*** | (2022.01) |
| ***B01J 8/00*** | (2006.01) |
| ***B01J 8/02*** | (2006.01) |
| ***B01J 20/285*** | (2006.01) |
| ***B01J 20/287*** | (2006.01) |
| ***B01J 20/32*** | (2006.01) |
| ***B01L 3/00*** | (2006.01) |
| ***B01L 9/00*** | (2006.01) |
| ***B65G 47/80*** | (2006.01) |
| ***B82Y 20/00*** | (2011.01) |
| ***B82Y 30/00*** | (2011.01) |
| ***B82Y 40/00*** | (2011.01) |
| ***C08L 5/08*** | (2006.01) |
| ***C12M 1/00*** | (2006.01) |
| ***C12M 1/34*** | (2006.01) |
| ***C12M 3/06*** | (2006.01) |
| ***C12N 1/14*** | (2026.01) |
| ***C12N 1/20*** | (2026.01) |
| ***C12Q 1/02*** | (2006.01) |
| ***C12Q 1/6806*** | (2018.01) |
| ***C12Q 1/6844*** | (2018.01) |
| ***C12Q 1/6848*** | (2018.01) |
| ***C12Q 1/6851*** | (2018.01) |
| ***C12Q 1/686*** | (2018.01) |
| ***G01K 1/14*** | (2021.01) |
| ***G01N 1/28*** | (2006.01) |
| ***G01N 1/44*** | (2006.01) |
| ***G01N 15/00*** | (2024.01) |
| ***G01N 15/01*** | (2024.01) |
| ***G01N 15/02*** | (2024.01) |
| ***G01N 15/10*** | (2024.01) |
| ***G01N 15/14*** | (2024.01) |
| ***G01N 15/1433*** | (2024.01) |
| ***G01N 21/01*** | (2006.01) |
| ***G01N 21/03*** | (2006.01) |
| ***G01N 21/05*** | (2006.01) |
| ***G01N 21/29*** | (2006.01) |
| ***G01N 21/33*** | (2006.01) |
| ***G01N 21/35*** | (2014.01) |
| ***G01N 21/59*** | (2006.01) |
| ***G01N 21/65*** | (2006.01) |
| ***G01N 21/75*** | (2006.01) |
| ***G01N 21/77*** | (2006.01) |
| ***G01N 27/07*** | (2006.01) |
| ***G01N 27/28*** | (2006.01) |
| ***G01N 27/416*** | (2006.01) |
| ***G01N 30/02*** | (2006.01) |
| ***G01N 30/60*** | (2006.01) |
| ***G01N 30/72*** | (2006.01) |
| ***G01N 31/10*** | (2006.01) |
| ***G01N 31/12*** | (2006.01) |
| ***G01N 33/543*** | (2006.01) |
| ***G01N 33/557*** | (2006.01) |
| ***G01N 33/564*** | (2006.01) |
| ***G01N 33/574*** | (2006.01) |
| ***G01N 33/575*** | (2026.01) |
| ***G01N 33/57515*** | (2026.01) |
| ***G01N 33/58*** | (2006.01) |
| ***G01N 33/68*** | (2006.01) |
| ***G01N 33/72*** | (2006.01) |
| ***G01N 35/00*** | (2006.01) |
| ***G01N 35/02*** | (2006.01) |
| ***H05B 45/10*** | (2020.01) |
| ***H10W 90/00*** | (2026.01) |

(52) U.S. Cl.

CPC . *G01N 15/0272* (2013.01); *B01D 2239/1208* (2013.01); *G01N 1/28* (2013.01); *G01N 2015/0053* (2013.01); *G01N 15/01* (2024.01)

(56) References Cited

U.S. PATENT DOCUMENTS

| | | | | |
|---|---|---|---|---|
| 9,273,275 | B2 | 3/2016 | Kobayashi | |
| 10,022,659 | B2 | 7/2018 | Ichinosawa et al. | |
| 10,473,567 | B2 | 11/2019 | Jeon et al. | |
| 2003/0134416 | A1 | 7/2003 | Yamanishi | |
| 2008/0248182 | A1 | 10/2008 | Jongsma et al. | |
| 2012/0183946 | A1 | 7/2012 | Tang | |
| 2013/0109086 | A1 | 5/2013 | Kobayashi | |
| 2013/0264272 | A1 | 10/2013 | Jeon et al. | |
| 2014/0023863 | A1 | 1/2014 | Gijsman | |
| 2014/0238863 | A1* | 8/2014 | Suzuki ................. | B01D 29/012 205/75 |
| 2014/0322747 | A1 | 10/2014 | Ito | |
| 2015/0111293 | A1* | 4/2015 | Kanbara ................. | G03F 7/405 156/60 |
| 2016/0136552 | A1 | 5/2016 | Nakanishi et al. | |
| 2017/0059460 | A1 | 3/2017 | Jeon et al. | |

FOREIGN PATENT DOCUMENTS

| | | | |
|---|---|---|---|
| JP | 2013541958 | A1 | 11/2013 |
| JP | 2014233209 | A | 12/2014 |
| JP | 201562400 | A | 4/2015 |
| JP | 2015188316 | A | 11/2015 |
| WO | 2012002497 | A1 | 1/2012 |
| WO | 2013093954 | A1 | 6/2013 |
| WO | 2013172265 | A1 | 11/2013 |
| WO | 2015012315 | A1 | 1/2015 |
| WO | 2013054786 | A1 | 3/2015 |

OTHER PUBLICATIONS

Written Opinion of the International Searching Authority issued in International Application No. PCT/JP2017/008145, date of mailing Apr. 4, 2017.

Masahito Hosokawa: "Size-Selective Microcavity Array for Rapid and Efficient Detection of Circulating Tumor Cells," Dept. of Biotechnology, Tokyo University of Agriculture and Tech., Feb. 24, 2016, Anal. Chem. 2010, 92, 5629-6635.

Japanese Office Action issued for JP 2019-086498, date of mailing Jun. 23, 2020. (English translation of Japanese Office Action is attached).

MONOist[online], Possibility of Also Detecting PM2.5, Murata Manufacturing Announces Standard Products of Metal Mesh Devices, Publication Date: Sep. 3, 2014, [Search Date: Jun. 9, 2020], <https://monoist.atmarkit.co.jp/mn/articles/1409/03/news128.html>.

(56) References Cited

OTHER PUBLICATIONS

PM 2.5 detection is also possible, Murata Manufacturing announces standard metal mesh device, published Sep. 3, 2014, https://monoist.atmarkit.co.jp/mn/articles/1409/03/news128.html ("Murata") (last visited Sep. 24, 2020). (Year: 2014).

* cited by examiner

METALLIC POROUS MEMBRANE, CLASSIFYING METHOD USING THE SAME, AND CLASSIFYING DEVICE

CROSS REFERENCE TO RELATED APPLICATIONS

The present application is a divisional of U.S. patent application Ser. No. 16/951,420, filed Nov. 18, 2020, which is a continuation of U.S. patent application Ser. No. 16/114,454, filed Aug. 28, 2018, which is a continuation of International application No. PCT/JP2017/008145, filed Mar. 1, 2017, which claims priority to Japanese Patent Application No. 2016-055475, filed Mar. 18, 2016, and Japanese Patent Application No. 2016-172839, filed Sep. 5, 2016, the entire contents of each of which are incorporated herein by reference.

FIELD OF THE INVENTION

The present invention relates to metallic porous membranes for classifying cell aggregates, and classifying methods as well as classifying device using the stated metallic porous membranes.

BACKGROUND OF THE INVENTION

In medicine efficacy research or the like using cell aggregates (spheroids), cell aggregates having a uniform dimension are required.

For example, Patent Document 1 discloses that cell aggregates are classified using a filter.

Patent Document 1: Japanese Unexamined Patent Application Publication No. 2015-62400

SUMMARY OF THE INVENTION

Recently, in the classification of cell aggregates using a filter, it has been requested to increase a collection rate of the cell aggregates.

An object of the present invention is to provide a metallic porous membrane capable of increasing a collection rate of cell aggregates, and a classifying method as well as a classifying device using the stated metallic porous membrane.

A metallic porous membrane according to an aspect of the present invention that classifies cell aggregates includes a membrane section having a first principal surface for capturing the cell aggregates, a second principal surface opposing the first principal surface, and a plurality of through-holes communicating with the first principal surface and the second principal surface.

A classifying method according to an aspect of the present invention that classifies cell aggregates includes preparing a metallic porous membrane provided with a membrane section including a first principal surface for capturing the cell aggregates, a second principal surface opposing the first principal surface, and a plurality of through-holes communicating with the first principal surface and the second principal surface; and classifying the cell aggregates, by passing a liquid containing the cell aggregates through the metallic porous membrane and capturing the cell aggregates on the metallic porous membrane.

A classifying device according to an aspect of the present invention that classifies cell aggregates includes a metallic porous membrane provided with a membrane section including a first principal surface for capturing the cell aggregates, a second principal surface opposing the first principal surface, and a plurality of through-holes communicating with the first principal surface and the second principal surface.

According to the aspects of the present invention, a metallic porous membrane capable of increasing a collection rate of cell aggregates, and a classifying method as well as a classifying device using the stated metallic porous membrane can be provided.

DETAILED DESCRIPTION OF THE PREFERRED EMBODIMENTS

(Reasons for Conceiving the Present Invention)

Figure 1:
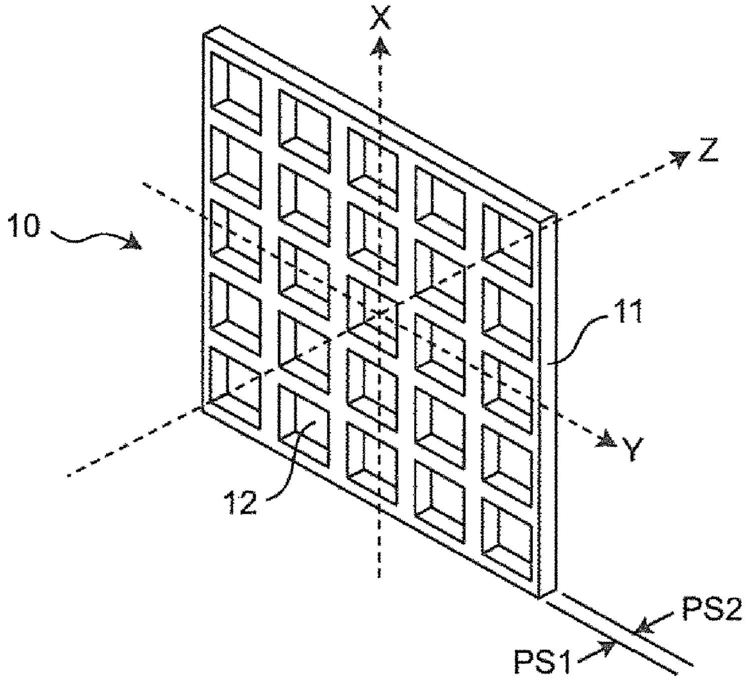
FIG. 1 is an enlarged perspective view illustrating part of a membrane section of a metallic porous membrane in a first embodiment according to the present invention.

In the case where medicine efficacy against cancer is researched, a cell aggregate is used as a model of a cancer cell, for example. Cancer cells have different sizes depending on the degree of advancement of cancer. Further, medicines effective against cancer differ depending on a difference in size of the cancer cells. For example, a medicine effective against early-stage cancer, small cancer tissue, or the like exhibits a small effect against advanced cancer, large cancer tissue, or the like in some case. Because of this, in medicine efficacy research using cell aggregates, if the medicine efficacy research is carried out using cell aggregates of different dimensions, a variation is generated in the medicine efficacy data. Accordingly, to suppress the variation in the medicine efficacy data, it is required to obtain cell aggregates having a uniform dimension.

Further, as for cell aggregates, they are typically used as tissue for regenerative medicine. In this case, although tissue having a desired size is needed, it is difficult to produce tissue having the desired size by devising a production method for cell aggregates. As such, it is more efficient to produce cell aggregates of various sizes and thereafter select the tissue of the desired size. Accordingly, it is required to select desired tissue with high efficiency.

As a method for adjusting the dimension of cultured cell aggregates to a desired dimension, for example, a method for classifying cell aggregates is used in which the cell aggregates having the desired dimension are captured using a filter made of a membrane, a nylon mesh, or the like. However, using the above-described filter raises a problem that a collection rate of the cell aggregates becomes low because dimension accuracy of the cell aggregates that can be captured is low. As such, the inventors of the present invention have conceived the invention as follows so as to solve the above problems.

A metallic porous membrane according to an embodiment of the present invention that classifies cell aggregates includes a membrane section having a first principal surface for capturing the cell aggregates, a second principal surface opposing the first principal surface, and a plurality of through-holes communicating with the first principal surface and the second principal surface.

With this configuration, the collection rate of the cell aggregates can be increased.

In the metallic porous membrane, the first principal surface of the membrane section may be formed to be flat, and the plurality of through-holes may each communicate through a wall surface continuously connecting an opening on the first principal surface side of the membrane section and an opening on the second principal surface side thereof.

With this configuration, the collection rate of the cell aggregates can be further increased.

In the above metallic porous membrane, the width of the through-hole may be less than 100% of the size of the cell aggregate.

With this configuration, the desired cell aggregates can be captured with certainty.

In the above metallic porous membrane, the width of the through-hole may be less than 80% of the size of the cell aggregate.

With this configuration, the desired cell aggregates can be captured with certainty even if the cell aggregates are deformed.

In the above metallic porous membrane, the width of the through-hole may be no less than 20% of the size of the cell aggregate.

This configuration makes it easy for a fluid that is not a capturing target to pass through, and consequently makes it possible to shorten a working time.

In the above metallic porous membrane, the width of the through-hole may be no less than 40% of the size of the cell aggregate.

This configuration makes it easier for a fluid that is not a capturing target to pass through, and consequently makes it possible to shorten the working time.

A classifying method for cell aggregates according to an embodiment of the present invention includes preparing a metallic porous membrane provided with a membrane section including a first principal surface for capturing the cell aggregates, a second principal surface opposing the first principal surface, and a plurality of through-holes communicating with the first principal surface and the second principal surface; and classifying the cell aggregates by passing a liquid containing the cell aggregates through the metallic porous membrane and capturing the cell aggregates on the metallic porous membrane.

With this configuration, the collection rate of the cell aggregates can be increased.

In the preparing of the metallic porous membrane in the classifying method, a plurality of metallic porous membranes respectively including through-holes having mutually different dimensions may be prepared, and the stated plurality of metallic porous membranes may be arranged in series from an upstream side of a flow path, through which a liquid containing the cell aggregates flows, in the descending order of the dimensions of the through-holes thereof.

With this configuration, the cell aggregates of the desired dimensions can be efficiently obtained in a stepwise manner.

In the classifying of the cell aggregates in the classifying method, isolated cells isolated from the cell aggregates may be allowed to pass through the metallic porous membrane positioned at the lowermost stage from among the plurality of metallic porous membranes.

With this configuration, a liquid not containing the cell aggregates but containing the isolated cells can be obtained.

The above-discussed classifying method may further include subculturing the isolated cells having passed through the metallic porous membrane positioned at the lowermost stage.

This configuration makes it possible for the isolated cells contained in the liquid having passed through the lowermost metallic porous membrane to be moved to a new culture medium and cultured therein. Alternatively, the isolated cells can also be used for forming cell aggregates again.

The above-discussed classifying method may further include washing the cell aggregates in a state of the stated cell aggregates being captured on the metallic porous membrane.

With this configuration, the classified cell aggregates can be washed with ease.

The classifying method may further include collecting the cell aggregates captured on the metallic porous membrane.

With this configuration, the classified cell aggregates can be collected with ease.

In the preparing of the metallic porous membrane in the classifying method, a sterilized metallic porous membrane may be prepared.

This configuration makes it possible to prevent the cell aggregates from being contaminated by bacterial adhering to the metallic porous membrane before the classification.

In the above-discussed classifying method, the flow path in which the liquid containing the cell aggregates flows while passing through the metallic porous membrane may be shut off from the outside air.

This configuration makes it possible to prevent the cell aggregates from being contaminated by the outside air.

A classifying device for cell aggregates according to an embodiment of the present invention includes a metallic porous membrane provided with a membrane section including a first principal surface for capturing the cell aggregates, a second principal surface opposing the first principal surface, and a plurality of through-holes communicating with the first principal surface and the second principal surface.

With this configuration, the collection rate of the cell aggregates can be increased.

In the classifying device, a plurality of metallic porous membranes respectively including through-holes having mutually different dimensions may be provided, and the stated plurality of metallic porous membranes may be arranged in series from an upstream side of a flow path, through which a liquid containing the cell aggregates flows, in the descending order of the dimensions of the through-holes thereof.

This configuration makes it possible to efficiently obtain the cell aggregates of the desired dimensions in the stepwise manner.

In the classifying device, the dimension of the through-holes of the metallic porous membrane positioned at the lowermost stage among the plurality of metallic porous membranes may be smaller than the size of the isolated cells isolated from the cell aggregates.

This configuration makes it possible to restrict the cell aggregates captured by the lowermost metallic porous membrane.

In the classifying device, the dimension of the through-holes of the metallic porous membrane positioned at the lowermost stage among the plurality of metallic porous membranes may be a size that can allow the isolated cells isolated from the cell aggregates to pass through.

With this configuration, a liquid not containing the cell aggregates but containing the isolated cells can be obtained.

The above-discussed classifying device may further be provided with a housing that encompasses the metallic porous membrane and includes a fluid introducing path provided so as to oppose the first principal surface of the metallic porous membrane as well as a fluid discharging path provided so as to oppose the second principal surface of the metallic porous membrane.

This configuration makes it possible to maintain the metallic porous membrane with ease and perform the classification at a high collection rate.

In the classifying device, the flow path in which the liquid containing the cell aggregates flows while passing through the metallic porous membrane may be shut off from the outside air.

This configuration makes it possible to prevent the cell aggregates from being contaminated by the outside air.

In the classifying device, the metallic porous membrane may be sterilized.

This configuration makes it possible to prevent the cell aggregates from being contaminated by bacterial adhering to the metallic porous membrane before the classification.

Hereinafter, a first embodiment according to the present invention will be described with reference to the accompanying drawings. Note that in the drawings, constitutive elements are illustrated in an exaggerated manner to assist with explanation thereof.

(First Embodiment)

[Metallic Porous Membrane]

FIG. 1 is an enlarged perspective view illustrating part of a metallic porous membrane 10 in a first embodiment according to the present invention. In FIG. 1, X, Y, and Z directions represent a longitudinal direction, a lateral direction, and a thickness direction of the metallic porous membrane 10, respectively. As illustrated in FIG. 1, the metallic porous membrane 10 is provided with a membrane section 11 that includes a first principal surface PS1 and a second principal surface PS2 opposing each other, and also includes a plurality of through-holes 12 passing through both the principal surfaces. The metallic porous membrane 10 is a plate-like structure (lattice-like structure) in which the plurality of through-holes 12 are provided at constant intervals in matrix form in the membrane section 11. The metallic porous membrane 10 is a metallic thin film configured to classify cell aggregates by passing a liquid containing a plurality of cell aggregates having different dimensions therethrough.

In the present specification, "cell aggregate" means aggregate mass of cells formed by a plurality of cells being bonded. The cell aggregate is, for example, a cell aggregate using cancerous cells, liver cells, iPS cells, or the like.

Although FIG. 1 does not illustrate the whole of the metallic porous membrane 10, the metallic porous membrane 10 is, for example, a circular metal mesh in the first embodiment. Dimensions of the metallic porous membrane 10 are, for example, 7.8 mm in diameter and 20 μm in thickness. A material configuring the metallic porous membrane 10 may be gold, silver, copper, platinum, nickel, stainless steel, palladium, titanium, or an alloy of these metals. In particular, as the material of the metallic porous membrane 10, gold, nickel, stainless steel, or titanium is preferable from the standpoint of a biological affinity for cell aggregates. The metallic porous membrane 10 is not limited to a circular shape, and may be formed in a rectangular shape such as a rectangle, square or the like, or a shape such as an oval or the like.

Figure 2:
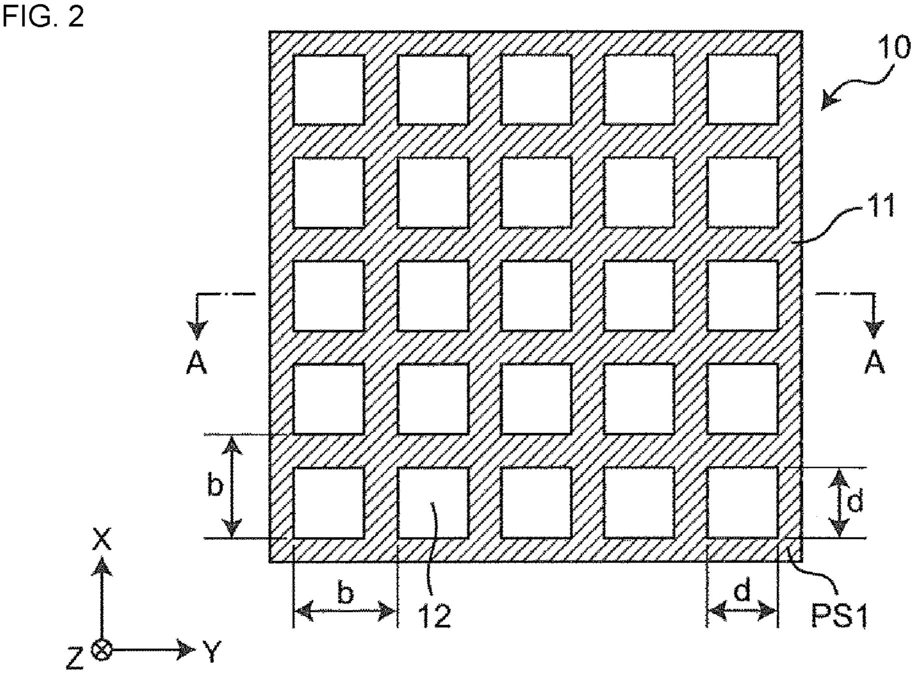
FIG. 2 is a schematic diagram illustrating part of the membrane section of the metallic porous membrane in FIG. 1 when viewed in a thickness direction thereof.

FIG. 2 is a schematic diagram illustrating part of the membrane section 11 of the metallic porous membrane 10 when viewed in the thickness direction (Z direction). As shown in FIG. 2, the plurality of through-holes 12 are periodically arranged on the first principal surface PS1 and the second principal surface PS2 of the membrane section 11. To be specific, the plurality of through-holes 12 are provided in the membrane section 11 at equal intervals in matrix form. The plurality of through-holes 12 are each formed in a square shape when viewed from the first principal surface PS1 side of the metallic porous membrane, in other words, when viewed in the Z direction. The plurality of through-holes 12 are provided at the equal intervals in two arrangement directions parallel to the sides of the square, in other words, arranged at the equal intervals in the X direction and the Y direction in FIG. 2. The through-holes 12 are not limited to a square shape, and may be formed in a shape such as a rectangle, circle, or oval. The arrangement of the holes are not limited to tetragonal lattice arrangement, and may be rectangle arrangement in which intervals in two arrangement directions are unequal in the case of square arrangement, triangle lattice arrangement, quasi-periodic arrangement, or the like, for example.

The shape and dimensions of the through-holes 12 should be appropriately designed in accordance with the size and shape of the cell aggregates. In the first embodiment, the through-hole 12 is formed in, for example, a square shape when viewed from the first principal surface PS1 side of the membrane section 11 of the metallic porous membrane 10, that is, when viewed in the Z direction; one side d thereof is designed to be less than 100% of the size of the cell aggregates. It is preferable that the one side d be designed to be less than 80% of the size of the cell aggregates, whereby the cell aggregates can be captured with certainty even if they are deformed during being filtered. Further, causing the one side d to be no less than 20% of the size of the cell aggregates makes it easy for a fluid that is not a capturing target to pass through, and consequently makes it possible to shorten the working time. It is more preferable to make the one side d be no less than 40% of the size of the cell aggregates, which makes it easier for the fluid to pass through. It is preferable for a lattice interval b between the through-holes 12 to be larger than one time (1×) the one side d of the through-hole 12 and no more than 10 times (10×) the one side d thereof, and is more preferable to be no more than three times (3×) the one side d of the through-hole 12, for example. Alternatively, it is preferable to be no less than 10% in terms of an opening ratio. The opening ratio is calculated by the division of (an area occupied by the through-holes 12)/(a projected entire area of the first principal surface PS1 including the area occupied by the through-holes 12). The through-holes 12 are not limited to a square shape, and may be formed in a shape such as a circle, oval, rectangle, or rhombus. In the first embodiment, although the dimension of the square through-hole 12 is explained using the one side d, the dimension of the through-hole 12 may be defined with a width of the through-hole 12. In the case where the through-hole 12 has a square shape, the width of the through-hole 12 corresponds to a line segment connecting two sides opposing each other, where a distance between the opposing two sides becomes longest. In the case where the through-hole 12 has a circular shape (including an oval shape), the width of the through-hole 12 corresponds to the diameter thereof.

The metallic porous membrane 10 includes the plurality of through-holes 12 having the same size. Here, "same size" means that a variation in dimension of the plurality of through-holes 12 falls within a range of ±5 μm. Some of the plurality of through-holes 12 may be formed having different dimensions. For example, in order to release pressure applied to the metallic porous membrane 10, some of the plurality of through-holes 12 may be formed having a larger dimension than that of the other through-holes to the extent that classification accuracy is not degraded.

In the present specification, when cell aggregates are disposed in a liquid and observed under a microscope, of lines respectively connecting two arbitrary points on an outer circumference of each cell aggregate in a two-dimensional observation image, the longest line is defined as a length of the cell aggregate, and an average value of the lengths of three or more capturing target cell aggregates is defined as a "size of the cell aggregate".

Figure 3:
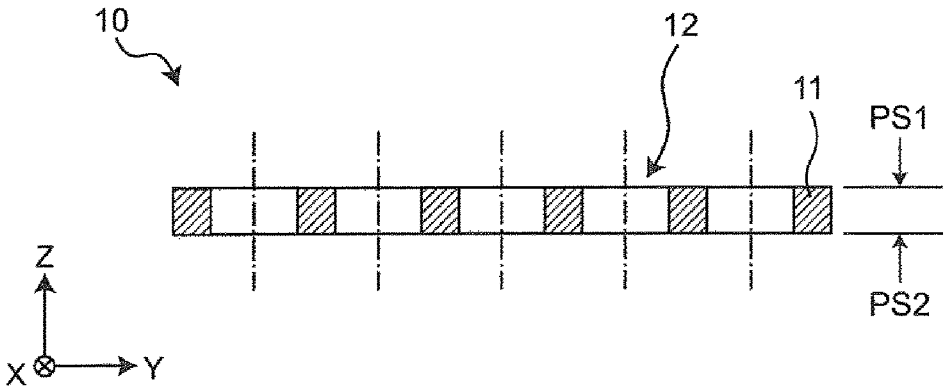
FIG. 3 is a cross-sectional view taken by cutting along an A-A line in FIG. 2.

FIG. 3 is a cross-sectional view illustrating part of the membrane section 11 of the metallic porous membrane 10 taken by cutting along an A-A line in FIG. 2. As shown in FIG. 3, the through-hole 12 communicates through a wall surface continuously connecting an opening on the first principal surface PS1 side of the membrane section 11 and an opening on the second principal surface PS2 side thereof. To be specific, the through-hole 12 is so provided that the opening on the first principal surface PS1 side can be projected on the opening on the second principal surface PS2 side. That is, in the case where the metallic porous membrane 10 is viewed from the first principal surface PS1 side, in other words, viewed in the Z direction, the through-hole 12 is so provided that the opening on the first principal surface PS1 side overlaps with the opening on the second principal surface PS2 side. In a preferred embodiment, the through-hole 12 is so provided that an inner wall thereof is perpendicular to the first principal surface PS1 and the second principal surface PS2. The size of the opening on the first principal surface PS1 side and the size of the opening on the second principal surface PS2 side may differ from each other.

Further, in the metallic porous membrane 10, the first principal surface PS1 of the membrane section 11 where the cell aggregates are captured is formed to be flat. That is, the first principal surface PS1 of the membrane section 11 is formed flush, and uneven portions in the Z direction are substantially not formed. In addition, the second principal surface PS2 of the membrane section 11 is also formed to be flat. Further, it is preferable for profile irregularity of both the principal surfaces of the membrane section 11 to be smaller than the size of the isolated cell. This is because it can be reduced that the isolated cells adhere to both the principal surfaces of the membrane section 11.

[Classifying Device]

Figure 4:
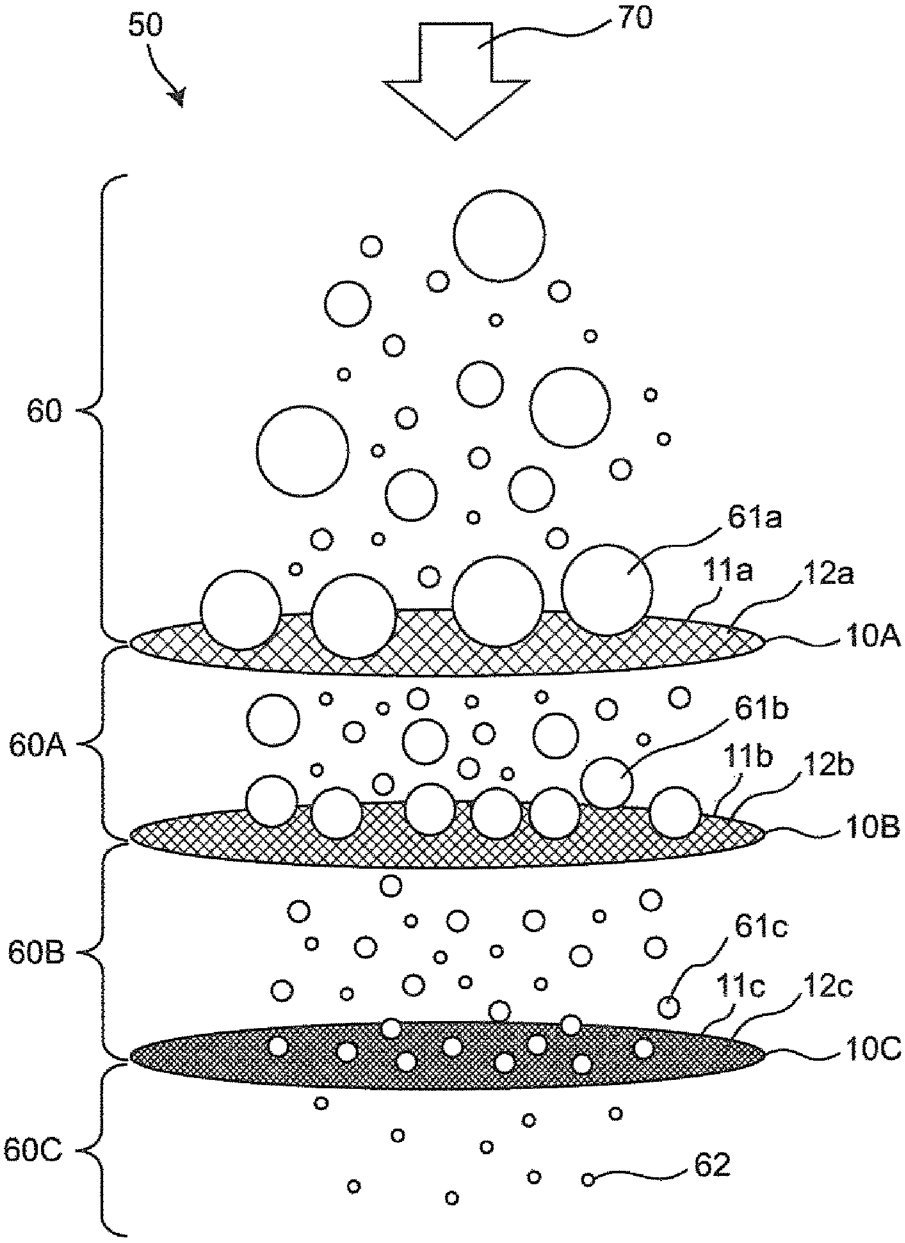
FIG. 4 is a schematic diagram illustrating a configuration of a classifying device of the first embodiment according to the present invention.

A classifying device according to the first embodiment of the present invention will be described with reference to FIG. 4. FIG. 4 is a schematic diagram illustrating a configuration of a classifying device 50 according to the first embodiment.

As shown in FIG. 4, the classifying device 50 is provided with a plurality of metallic porous membranes 10A, 10B, and 10C. The plurality of metallic porous membranes 10A, 10B, and 10C are arranged in series in a direction 70 in which a liquid 60 containing cell aggregates 61*a*, 61*b*, 61*c* and isolated cells 62 flows. In the first embodiment, the metallic porous membranes 10A, 10B, and 10C are disposed in that order from an upstream side in a flow path through which the liquid 60 flows. In other words, in the classifying device 50, the metallic porous membrane 10A is disposed at the uppermost stage, the metallic porous membrane 10B is disposed at the center stage, and the metallic porous membrane 10C is disposed at the lowermost stage. Further, the metallic porous membranes 10A, 10B, and 10C are disposed so that each first principal surface PS1 thereof is orthogonal to the direction 70 in which the liquid 60 flows.

In the first embodiment, the cell aggregates 61*a*, 61*b*, and 61*c* are cell aggregates having mutually different dimensions. The cell aggregate 61*a* has a larger dimension than the cell aggregate 61*b*, and the cell aggregates 61*b* has a larger dimension than the cell aggregate 61*c*. In other words, of the cell aggregates 61*a*, 61*b*, and 61*c*, the cell aggregate 61*a* is largest while the cell aggregate 61*c* is smallest.

In the present specification, an "isolated cell" refers to one cell that forms a cell aggregate and is in an independent state in which it does not adhere to the cell aggregate. In other words, the "isolated cell" means a cell isolated from the cell aggregate. Alternatively, the "isolated cell" means an isolated cell that has not been involved in forming the cell aggregate. In the first embodiment, the dimension of the isolated cell 62 is smaller than the dimension of each of the cell aggregates 61*a*, 61*b*, and 61*c*.

Through-holes 12*a*, 12*b*, and 12*c* having mutually different dimensions are respectively provided in membrane sections 11*a*, 11*b*, and 11*c* of the metallic porous membranes 10A, 10B, and 10C. The through-hole 12*a* has a larger dimension than the through-hole 12*b*, and the through-hole 12*b* has a larger dimension than the through-hole 12*c*. In other words, of the through-holes 12*a*, 12*b*, and 12*c*, the through-hole 12*a* has the largest dimension while the through-hole 12*c* has the smallest dimension.

The through-hole 12*a* of the metallic porous membrane 10A is designed with a dimension that does not allow the cell aggregate 61*a* to pass through but allows the cell aggregates 61*b*, 61*c* and the isolated cell 62 to pass through. Specifically, the through-hole 12*a* is designed with the dimension smaller than the cell aggregate 61*a* and larger than the cell aggregate 61*b*. Because of this, in the case where the liquid 60 containing the cell aggregates 61*a*, 61*b*, 61*c* and the isolated cells 62 is filtered by passing through the metallic porous membrane 10A, the cell aggregates 61*a* cannot pass through the through-holes 12*a* and are captured on the first principal surface PS1 of the metallic porous membrane 10A. That is, the cell aggregates 61*a* larger than the dimension of the through-holes 12*a* are captured on the first principal surface PS1 of the metallic porous membrane 10A. On the other hand, the cell aggregates 61*b*, 61*c* and the isolated cells 62 contained in the liquid 60 can pass through the through-holes 12*a*. Because of this, a liquid (filtrate) 60A after being filtered by the metallic porous membrane 10A contains the cell aggregates 61*b*, 61*c* and the isolated cells 62, but does not contain the cell aggregates 61*a*. Accordingly, with the metallic porous membrane 10A, the cell aggregates 61*a* can be classified from the liquid 60 containing the cell aggregates 61*a*, 61*b*, 61*c* and the isolated cells 62.

The through-hole 12*b* of the metallic porous membrane 10B is designed with a dimension that does not allow the cell aggregate 61*b* to pass through but allows the cell aggregate 61*c* and the isolated cell 62 to pass through. Specifically, the through-hole 12*b* is designed with the dimension smaller than the cell aggregate 61*b* and larger than the cell aggregate 61*c*. Because of this, in the case where the liquid 60A having been filtered by the metallic porous membrane 10A is filtered by passing through the metallic porous membrane 10B, the cell aggregates 61*b* cannot pass through the through-holes 12*b* and are captured on the first principal surface PS1 of the metallic porous membrane 10B. On the other hand, the cell aggregates 61*c* and the isolated cells 62 contained in the liquid 60A can pass through the through-holes 12*b*. Because of this, a liquid (filtrate) 60B after being filtered by the metallic porous membrane 10B contains the cell aggregates 61*c* and the isolated cells 62, but does not contain the cell aggregates 61*b*. Accordingly, with the metallic porous membrane 10B, the cell aggregates 61*b* can be classified from the liquid 60A containing the cell aggregates 61*b*, 61*c* and the isolated cells 62.

The through-hole 12C of the metallic porous membrane 10C is designed with a dimension that does not allow the cell aggregate 61*c* to pass through but allows the isolated cell 62 to pass through. Specifically, the through-hole 12*c* is designed with the dimension smaller than the cell aggregate 61*c* and larger than the isolated cell 62. Because of this, in the case where the liquid 60B having been filtered by the metallic porous membrane 10B is filtered by passing through the metallic porous membrane 10C, the cell aggregates 61*c* cannot pass through the through-holes 12*c* and are captured on the first principal surface PS1 of the metallic porous membrane 10C. On the other hand, the isolated cells 62 contained in the liquid 60B can pass through the through-holes 12*c*. Because of this, a liquid (filtrate) 60C after being filtered by the metallic porous membrane 10C contains the isolated cells 62, but does not contain the cell aggregates 61*c*. Accordingly, with the metallic porous membrane 10C, the cell aggregates 61*c* can be classified from the liquid 60B containing the cell aggregates 61*c* and the isolated cells 62.

The isolated cells 62 contained in the liquid (filtrate) 60C after being filtered by the metallic porous membrane 10C can be subcultured. Alternatively, they can be used for producing other cell aggregates.

As discussed above, in the classifying device 50, the plurality of metallic porous membranes 10A, 10B, and 10C are arranged in series from the upstream side of the flow path, through which the liquid 60 flows, in the descending order of the dimensions of the through-holes 12*a*, 12*b*, and 12*c* thereof. This configuration makes it possible to classify the cell aggregates having the desired dimensions in the stepwise manner from the liquid 60 containing the cell aggregates 61*a*, 61*b*, 61*c* and the isolated cells 62 having mutually different dimensions.

The classifying device 50 may be provided with a housing for holding the metallic porous membranes 10A, 10B, and 10C. In this case, the classifying device 50 filters out filtering target objects contained in a fluid, having been introduced through a fluid introducing path, by the metallic porous membranes 10A, 10B, and 10C housed in the housing in which the fluid introducing path and a fluid discharging path are provided, and discharges the fluid having passed through the above metallic porous membranes from the fluid discharging path.

Figure 5:
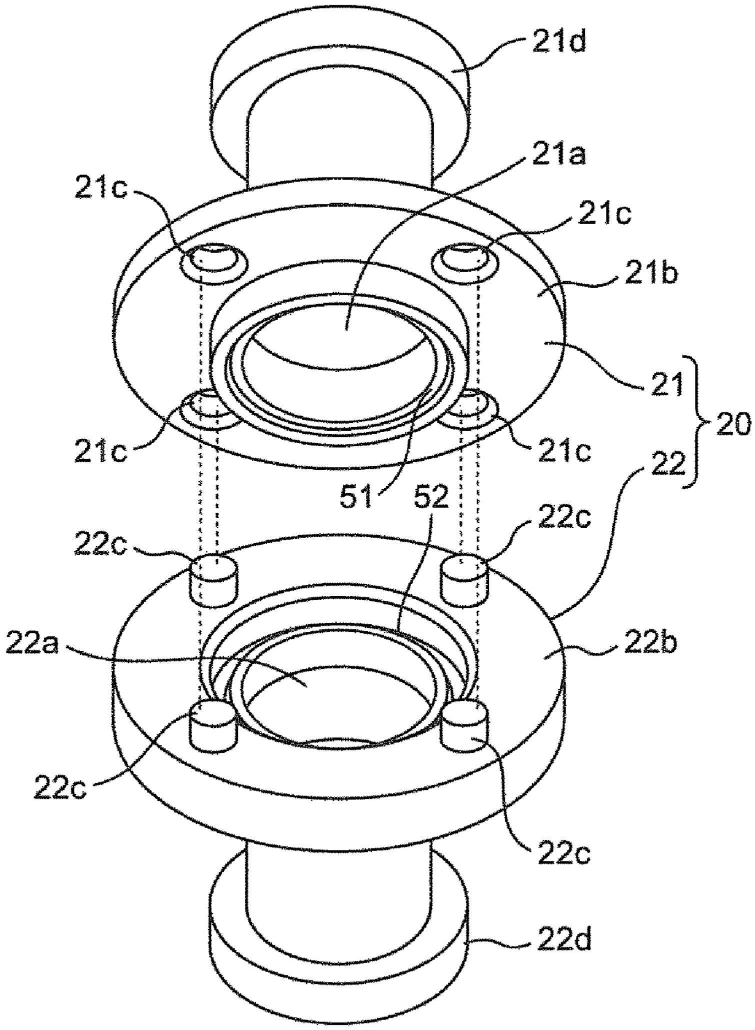
FIG. 5 is a perspective view illustrating a housing of the classifying device of the first embodiment according to the present invention.
Figure 6:
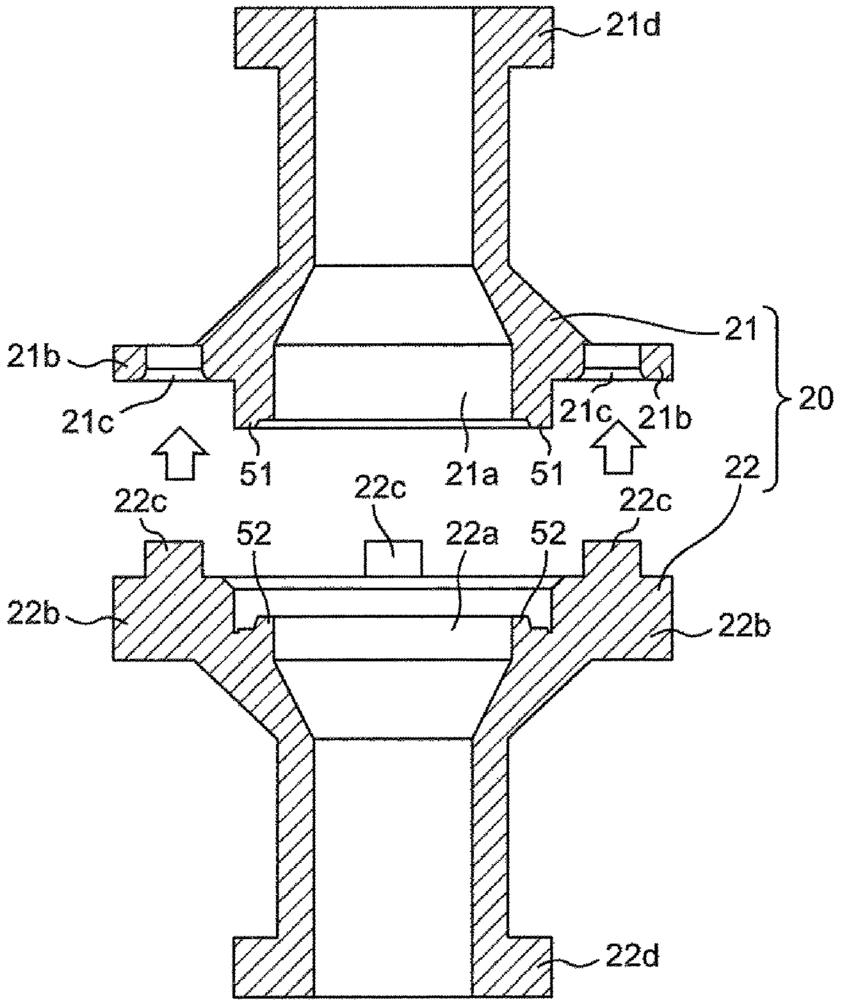
FIG. 6 is a perspective view in which a cross section of part of the housing in FIG. 5 is illustrated.

FIG. 5 is an exploded perspective view illustrating a general structure of a housing 20 for holding the metallic porous membrane 10A, and FIG. 6 is an exploded cross-sectional view thereof. Note that in FIGS. 5 and 6, the metallic porous membrane 10A is not illustrated.

As shown in FIGS. 5 and 6, the housing 20 includes a first housing section 21 formed in a substantially cylindrical shape and a second housing section 22 also formed in a substantially cylindrical shape.

The first housing section 21 includes a fluid introducing path 21*a* that is so provided as to oppose the first principal surface PS1 of the metallic porous membrane 10A. The first housing section 21 is integrally formed with a first frame member 51 pinching an outer circumference portion of the metallic porous membrane 10A. In other words, the first frame member 51 is configured as part of the first housing section 21. An inner diameter of the first frame member 51 is 6.0 mm, for example.

On the periphery of the first frame member 51 of the first housing section 21, there is formed a flange section 21*b* extending in a direction intersecting with (for example, orthogonal to) an extension direction of the fluid introducing path 21*a*. A plurality of through-holes 21*c* are formed in the flange section 21*b* passing through in a thickness direction of the flange section 21*b*. In the first embodiment, the plurality of through-holes 21*c* of four are formed at an interval of 90 degrees. The thickness of the flange section 21*b* is, for example, 2.1 mm. The diameter of the through-hole 21*c* is, for example, 1.42 mm. The length of the through-hole 21*c* is, for example, 0.9 mm.

The second housing section 22 includes a fluid discharging path 22*a* that is so provided as to oppose the second principal surface PS2 of the metallic porous membrane 10A. The second housing section 22 is integrally formed with a second frame member 52 pinching the outer circumference portion of the metallic porous membrane 10A. In other words, the second frame member 52 is configured as part of the second housing section 22. An inner diameter of the second frame member 52 is 6.0 mm, for example.

On the periphery of the second frame member 52 of the second housing section 22, there is formed a flange section 22*b* extending in a direction intersecting with (for example, orthogonal to) the extension direction of the fluid discharging path 22*a*. A plurality of projections 22*c* are formed on the flange section 22*b* projecting in the thickness direction of the flange section 22*b*. In the first embodiment, the plurality of projections 22*c* of four are formed at an interval of 90 degrees. The diameter of the projection 22*c* is, for example, 1.4 mm. The height of the projection 22*c* is, for example, 0.9 mm.

The first housing section 21 and the second housing section 22 are so configured as to be fitted to each other by the plurality of projections 22*c* being inserted into the plurality of through-holes 21*c*. By the first housing section 21 and the second housing section 22 being fitted to each other, the outer circumference portion of the metallic porous membrane 10A is held between the first frame member 51 and the second frame member 52.

The housing 20 can be used while being attached to a luer-lock type syringe (not illustrated), for example. In this case, it is sufficient to provide a ridge or the like, capable of being connected with the luer-lock type syringe, to at least one of a terminal end portion 21*d* (upper end portion in FIG. 6) of the first housing section 21 and a terminal end portion 22*d* (lower end portion in FIG. 6) of the second housing section 22.

In the classifying device 50, the flow path through which the liquids 60, 60A, 60B, and 60C flow may be shut off from the outside air. As discussed above, by shutting off the liquids 60, 60A, 60B, and 60C from the outside air, the cell aggregates 61*a*, 61*b*, 61*c*, and the isolated cells 62 contained in the liquids 60, 60A, 60B, and 60C can be prevented from being contaminated.

[Classifying Method]

Figure 7:
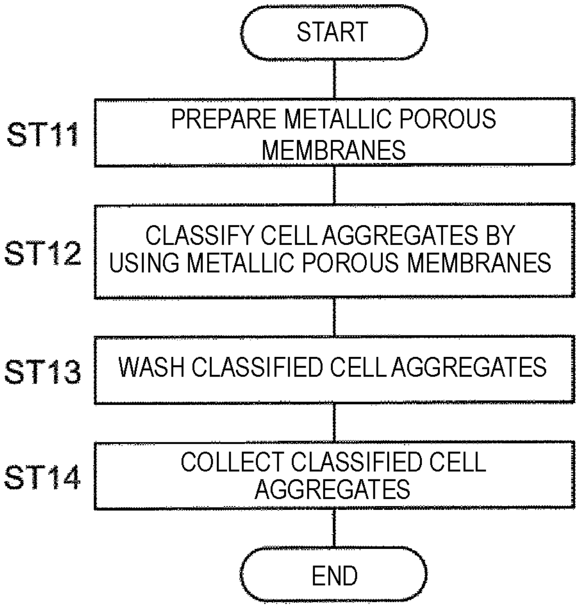
FIG. 7 is a flowchart of a classifying method of the first embodiment according to the present invention.

A classifying method according to the first embodiment of the present invention will be described with reference to FIG. 7. FIG. 7 is a flowchart illustrating the classifying method according to the first embodiment.

The classifying method according to the first embodiment classifies the liquid 60 containing the cell aggregates 61*a*, 61*b*, 61*c* and the isolated cells 62, using the plurality of metallic porous membranes 10A, 10B, and 10C, into the cell aggregates 61*a*, 61*b*, 61*c* and the isolated cells 62, respectively.

As shown in FIG. 7, the plurality of metallic porous membranes 10A, 10B, and 10C are prepared in a step ST11. Specifically, the metallic porous membranes 10A, 10B, and 10C are arranged in that order from the upstream in the flow path through which the liquid 60 flows (see FIG. 4). The metallic porous membranes 10A, 10B, and 10C are not described herein because the configurations thereof are the same as those in the above-described classifying device 50.

The metallic porous membranes 10A, 10B, and 10C prepared in the step ST11 may have experienced a sterilization process. The sterilization process includes, for example, gamma-ray sterilization by gamma-ray irradiation, autoclave sterilization by saturated water vapor at high temperature and high pressure, ethylene oxide gas sterilization using an ethylene oxide gas, oxidation sterilization by ozone, or the like.

In a step ST12, by using the metallic porous membranes 10A, 10B, and 10C, the cell aggregates 61*a*, 61*b*, and 61*c* are respectively classified. In the step ST12, the liquid 60 containing the cell aggregates 61*a*, 61*b*, 61*c* and the isolated cells 62 is filtered by passing through the metallic porous membranes 10A, 10B, and 10C.

To be more specific, the liquid 60 is filtered by passing through the metallic porous membrane 10A first. By the liquid 60 being filtered by the metallic porous membrane 10A, the cell aggregates 61*a* larger than the dimension of the through-holes 12*a* are captured on the first principal surface PS1 of the metallic porous membrane 10A. Through this, the cell aggregates 61*a* are classified.

Next, a filtrate obtained after being filtered by the metallic porous membrane 10A, that is, the liquid 60A containing the cell aggregates 61*b*, 61*c* and the isolated cells 62 is filtered by passing through the metallic porous membrane 10B disposed on a downstream side relative to the metallic porous membrane 10A. By the liquid 60A being filtered by the metallic porous membrane 10B, the cell aggregates 61*b* larger than the dimension of the through-holes 12*b* are captured on the first principal surface PS1 of the metallic porous membrane 10B. Through this, the cell aggregates 61*b* are classified.

Next, the filtrate obtained after being filtered by the metallic porous membrane 10B, that is, the liquid 60B containing the cell aggregates 61*c* and the isolated cells 62 is filtered by passing through the metallic porous membrane 10C disposed on the downstream side relative to the metallic porous membrane 10B. By the liquid 60B being filtered by the metallic porous membrane 10C, the cell aggregates 61*c* larger than the dimension of the through-holes 12*c* are captured on the first principal surface PS1 of the metallic porous membrane 10C. Through this, the cell aggregates 61*c* are classified.

Further, by the liquid 60B being filtered by the metallic porous membrane 10C, the liquid 60C containing the isolated cells 62 can be obtained as the filtrate. The isolated cells 62 taken out from the liquid 60C can be subcultured. In other words, the isolated cells 62 contained in the liquid 60C can be moved to a new culture medium and cultured again therein.

In a step ST13, the cell aggregates 61*a*, 61*b*, and 61*c* captured by the metallic porous membranes 10A, 10B, and 10C, respectively, are washed using a washing fluid. For example, by flowing the washing fluid in the direction 70 in which the liquid 60 flows, the cell aggregates 61*a*, 61*b*, and 61*c* are washed in a state of being captured by the metallic porous membranes 10A, 10B, and 10C. The washing method for the cell aggregates 61*a*, 61*b*, and 61*c* is not limited thereto, and various kinds of washing methods may be used. The step ST13 may be omitted.

In a step ST14, the cell aggregates 61*a*, 61*b*, and 61*c* respectively captured by the metallic porous membranes 10A, 10B, and 10C are collected. For example, the metallic porous membrane 10A in a state of capturing the cell aggregates 61*a*is detached, set in a culture medium, and then vibrated in the thickness direction of the metallic porous membrane 10A. Through this, the cell aggregates 61*a* having been captured by the metallic porous membrane 10A can be isolated from the first principal surface PS1 of the metallic porous membrane 10A and collected. Alternatively, by passing a fluid for collection through the through-holes 12*a* in a direction from the second principal surface PS2, to which the cell aggregates 61*a* are not attached, toward the first principal surface PS1, the cell aggregates 61*a* can be isolated from the first principal surface PS1 of the metallic porous membrane 10A and collected. The collecting method for the cell aggregates 61*a*, 61*b*, and 61*c* is not limited thereto, and various kinds of collecting methods may be used.

The cell aggregates 61*a*, 61*b*, and 61*c* collected in the manner described above are used for medicine efficacy researches. For example, in the case of researching medicine efficacy against cancer, the cell aggregate 61*c* smaller in dimension than the cell aggregates 61*a* and 61*b* is used in the medicine efficacy research against early-stage cancer. In contrast, the medicine efficacy research against advanced cancer is carried out using the cell aggregate 61*a*.

[Effects]

With the metallic porous membrane 10 according to the first embodiment, the following effects can be obtained.

The metallic porous membrane 10 is provided with the membrane section 11 including the first principal surface PS1 for capturing cell aggregates 61, the second principal surface PS2 opposing the first principal surface PS1, and the plurality of through-holes 12 communicating with the first principal surface PS1 and the second principal surface PS2. With this configuration, since the dimension accuracy when classifying the cell aggregates 61 can be enhanced, the collection rate of the cell aggregates 61 can be increased.

The metallic porous membrane 10 has a higher rigidity than a filter made of a membrane, nylon mesh, or the like. Because of this, in the metallic porous membrane 10, in the case of filtering the liquid 60 containing the cell aggregates 61, the through-holes 12 are unlikely to be deformed compared to the filter made of a membrane, nylon mesh, or the like even if the pressure due to the liquid 60 is applied to the first principal surface PS1 of the membrane section 11.

Accordingly, the metallic porous membrane 10 can capture the cell aggregates 61 larger than the through-holes 12 on the first principal surface PS1 of the metallic porous membrane 10 with certainty in comparison with the filter made of a membrane, nylon mesh, or the like. Because through-holes of the filter made of a membrane, nylon mesh, or the like are likely to be deformed in the case where the pressure due to the liquid 60 is applied to a membrane surface thereof, there is a case in which the cell aggregates 61 larger than the through-holes pass through the filter.

In the metallic porous membrane 10, the through-hole 12 communicates through a wall surface continuously connecting an opening on the first principal surface PS1 side of the membrane section 11 and an opening on the second principal surface PS2 side thereof. Further, the through-hole 12 is so provided that the opening on the first principal surface PS1 side of the membrane section 11 can be projected on the opening on the second principal surface PS2 side thereof. With this configuration, the cell aggregate 61 smaller than the through-hole 12 is likely to pass through the through-hole 12. In a membrane filer, because the though-hole does not communicate through a side wall continuously connecting an opening on a first principal surface side of a membrane section and an opening on a second principal surface side thereof, the cell aggregate 61 smaller than the through-hole 12 is unlikely to pass through the through-hole. Because of this, in the membrane filter, the cell aggregates 61 are caused to remain in the filter.

Further, in the metallic porous membrane 10, the first principal surface PS1 of the membrane section 11 where the cell aggregates 61 are captured is formed to be flat. That is, the first principal surface PS1 of the membrane section 11 of the metallic porous membrane 10 is formed flush. With this configuration, the cell aggregate 61 smaller than the through-hole 12 of the metallic porous membrane 10 is likely to be introduced into the through-hole 12. Further, when the cell aggregates 61 captured on the first principal surface PS1 of the membrane section 11 of the metallic porous membrane 10 are collected, the cell aggregates 61 can be isolated with ease from the first principal surface PS1 of the membrane section 11. In the filter made of a membrane, nylon mesh, or the like, uneven portions are formed in the first principal surface of the membrane section where the cell aggregates 61 are captured. As such, because even the cell aggregate 61 smaller than the through-hole is caught by the uneven portions in some case, there is a case in which the cell aggregate 61 having a dimension other than the desired dimension is collected. In addition, when collecting the cell aggregates 61, the cell aggregates 61 may be caught by the uneven portions.

The metallic porous membrane 10 is not changed even by flame sterilization and has high thermal conductivity, thereby making it possible to obtain a high sterilization effect.

As discussed above, the metallic porous membrane 10 is configured such that the cell aggregates 61 larger than the through-holes 12 can be more surely captured and the cell aggregates 61 smaller than the through-holes 12 are likely to be introduced into the through-holes 12. Further, with the metallic porous membrane 10, the cell aggregates 61 can be isolated with ease from the first principal surface PS1 of the membrane section 11 and collected. This makes it possible for the metallic porous membrane 10 to increase the dimension accuracy of the cell aggregates 61 to be classified and increase the collection rate in comparison with the filter made of a membrane, nylon mesh, or the like.

With the classifying device 50 according to the first embodiment, the following effects can be obtained.

According to the classifying device 50, since the cell aggregates 61 are classified using the above-described metallic porous membrane 10, the collection rate of the cell aggregates 61 can be increased.

The classifying device 50 is provided with the metallic porous membranes 10A, 10B, and 10C respectively including the through-holes 12*a*, 12*b*, and 12*c* having mutually different dimensions. The plurality of metallic porous membranes 10A, 10B, and 10C are arranged in series from the upstream side of the flow path, through which the liquid 60 containing the cell aggregates 61*a*, 61*b*, and 61*c* flows, in the descending order of the dimensions of the through-holes 12*a*, 12*b*, and 12*c*. This configuration makes it possible to classify the cell aggregates 61*a*, 61*b*, and 61*c* from the liquid 60 using the plurality of metallic porous membranes 10A, 10B, and 10C, respectively. That is, according to the classifying device 50, the cell aggregates 61*a*, 61*b*, and 61*c* having mutually different dimensions can be obtained in the stepwise manner. Further, with the classifying device 50, the cell aggregates 61*a*, 61*b*, and 61*c* which the metallic porous membrane on the upstream side failed to capture can be collected by the metallic porous membrane on the downstream side with certainty.

In the classifying device 50, the dimension of the through-hole 12*c* of the metallic porous membrane 10C positioned at the lowermost stage is so designed as to allow the isolated cell 62 to pass through. With this configuration, the liquid 60C containing the isolated cells 62 can be obtained after having classified the cell aggregates 61*a*, 61*b*, and 61*c*. This makes it possible for the isolated cells 62 to be subcultured. In other words, by the isolated cells 62 being moved to a new culture medium and cultured again, life or death of the cells can be determined, for example. Alternatively, the isolated cells 62 can also be used for producing other cell aggregates.

In the classifying device 50, the metallic porous membranes 10A, 10B, and 10C can each be housed in the housing 20 that includes the fluid introducing path 21*a* provided so as to oppose the first principal surface PS1 of the metallic porous membrane and the fluid discharging path 22*a* provided so as to oppose the second principal surface PS2 of the metallic porous membrane. This configuration makes it possible to hold each of the metallic porous membranes 10A, 10B, and 10C with ease in the housing 20 including the fluid introducing path 21*a* and the fluid discharging path 22*a*. Because the first frame member 51 and the second frame member 52 pinching the outer circumference portion of each of the metallic porous membranes 10A, 10B, and 10C are integrally formed with the first housing section 21 and the second housing section 22, respectively, the number of components of the classifying device 50 can be reduced.

With the classifying method according to the first embodiment, the following effects can be obtained.

According to the classifying method, since the cell aggregates 61 are classified using the above-described metallic porous membrane 10, the collection rate of the cell aggregates 61 can be increased. Further, the stated classifying method has the same effects as the above-discussed classifying device 50.

In the classifying method, the cell aggregates 61*a*, 61*b*, and 61*c* can be washed in a state of being captured by the metallic porous membranes 10A, 10B, and 10C. For example, by flowing the washing fluid in the direction 70 in which the liquid 60 flows, the cell aggregates 61*a*, 61*b*, and 61*c* captured by the metallic porous membranes 10A, 10B, and 10C can be washed. This makes it possible to easily wash the classified cell aggregates 61$a$, 61$b$, and 61$c$.

In the classifying method, for example, by vibrating or the like of the metallic porous membranes 10A, 10B, and 10C respectively capturing the cell aggregates 61$a$, 61$b$, and 61$c$ in the thickness direction of the metallic porous membranes 10A, 10B, and 10C in a culture medium, the cell aggregates 61$a$, 61$b$, and 61$c$ can be collected with ease. Alternatively, by passing a fluid for collection through the through-holes 12$a$ in a direction from the second principal surface PS2, to which the cell aggregates 61$a$ are not attached, toward the first principal surface PS1, the cell aggregates 61$a$ can be isolated from the first principal surface PS1 of the metallic porous membrane 10A and collected. In this manner, the cell aggregates 61$a$, 61$b$, and 61$c$ respectively captured by the metallic porous membranes 10A, 10B, and 10C can be easily isolated from the metallic porous membranes 10A, 10B, and 10C.

In the classifying method, medicine efficacy researches can be carried out using the classified cell aggregates 61$a$, 61$b$, and 61$c$. Because the classified cell aggregates 61$a$, 61$b$, and 61$c$ respectively have uniform dimensions, variations in medicine efficacy research data can be reduced.

Although the configuration of the classifying device 50 including the plurality of metallic porous membranes 10A, 10B, and 10C is described in the first embodiment, the embodiment is not limited thereto. The classifying device 50 may include at least one or more metallic porous membranes 10. Although the configuration in which the plurality of metallic porous membranes 10A, 10B, and 10C respectively include the through-holes 12$a$, 12$b$, and 12$c$ having mutually different dimensions has been described thus far, the configuration is not limited thereto. For example, the plurality of metallic porous membranes 10A, 10B, and 10C may include the through-holes 12 having the same dimension. With the above configuration, the cell aggregates 61$a$ which the metallic porous membrane 10A on the upstream side failed to capture can be captured by the metallic porous membrane 10B on the downstream side.

Although the configuration in which the through-hole 12$c$ of the metallic porous membrane 10C positioned at the lowermost stage is designed with a dimension that allows the isolated cell 62 to pass through is described in the first embodiment, the embodiment is not limited thereto. The through-hole 12$c$ of the metallic porous membrane 10C may be designed to have a size equal to or smaller than that of the isolated cell 62 isolated from the cell aggregates, for example. That is, the through-hole 12$c$ of the metallic porous membrane 10C may be designed with the same dimension as that of the isolated cell 62, or designed with a dimension smaller than that of the isolated cell 62.

Although the first housing section 21 and the second housing section 22 are so configured as to be fitted to each other by the plurality of projections 22$c$ being inserted into the plurality of through-holes 21$c$ in the first embodiment, the present invention is not limited thereto. For example, the configuration may be as follows: that is, a plurality of through-holes are provided in the first housing section 21 and a plurality of projections are provided on the second housing section 22, and then the plurality of projections are inserted into the plurality of through-holes, whereby the first housing section 21 and the second housing section 22 are fitted to each other. It is sufficient that the first housing section 21 and the second housing section 22 are so configured as to be fitted to each other.

Although the configuration in which the first frame member 51 and the second frame member 52 are integrally formed with the first housing section 21 and the second housing section 22, respectively, is described in the first embodiment, the embodiment is not limited thereto. For example, the first frame member 51 and the second frame member 52 may be configured of different materials from those of the first housing section 21 and the second housing section 22.

Working examples will hereinafter be described.

(First Working Example)

In a first working example, the cell aggregates 61 were classified using the metallic porous membrane 10 of the first embodiment. As a first comparative example, the cell aggregates 61 were classified using a nylon mesh.

Figure 8:
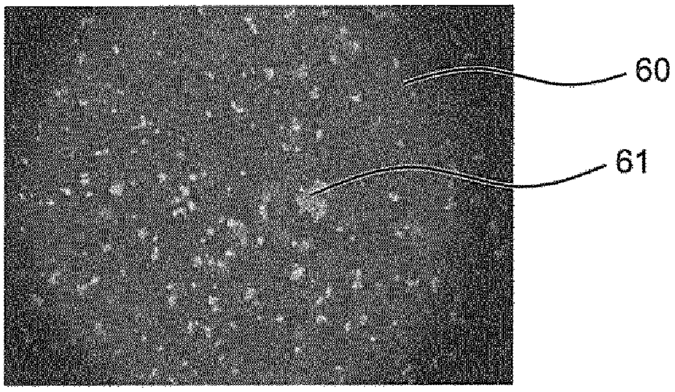
FIG. 8 is a photograph showing a liquid containing cell aggregates having different sizes.

In the first working example and the first comparative example, the liquid 60 containing the cell aggregates 61 is shown in FIG. 8. As shown in FIG. 8, the liquid 60 contains the plurality of cell aggregates 61 having different dimensions.

The cell aggregates 61 shown in FIG. 8 were produced in a manner in which a cell suspension solution in a fluid volume of 0.2 ml containing NIH3T3/ras was disseminated in a dish with a diameter being 35 mm and cultured for a day in a general incubator. In this case, a culture medium was 3 ml in volume and a total number of cell aggregates was approximately $1\times10^5$.

In the first working example, the metallic porous membrane 10 of the first embodiment was used. The metallic porous membrane 10 is a circular mesh made of nickel. The outer diameter of the metallic porous membrane 10 is 7.8 mm, and the membrane section 11 with a diameter of 6 mm is formed in a center portion of the metallic porous membrane 10. In the membrane section 11, the through-holes 12 formed in a square shape are provided in tetragonal lattice arrangement. One side of the through-hole 12 is 120 μm in length. An interval between the through-holes 12, that is, a distance of a metal portion between two through-holes 12, 12 is 50 μm. To rephrase, a lattice interval between the through-holes 12 is 170 μm. The thickness is 17 μm. The metallic porous membrane 10 has experienced a sterilization process by gamma-irradiation before the classification is performed. In the first working example, the liquid 60 containing the cell aggregates 61 having different dimensions as shown in FIG. 8 was made to pass through the metallic porous membrane 10 to be filtered, whereby the cell aggregates 61 were classified.

A nylon mesh was used in the first comparative example. The nylon mesh is a circular mesh made of nylon 6.6. The outer diameter of the nylon mesh is 7.8 mm, and a membrane section is formed in the center portion. In the membrane section, square through-holes are provided in tetragonal lattice arrangement. One side of the through-hole is 131 μm in length. An interval between the through-holes, that is, a wire diameter of the nylon mesh is 72 μm. To rephrase, a lattice interval between the through-holes is 203 μm. The nylon mesh has not experienced the sterilization process because the nylon mesh itself is damaged when being irradiated with gamma rays. In the first comparative example, the liquid 60 containing the cell aggregates 61 having different dimensions as shown in FIG. 8 was made to pass through the nylon mesh to be filtered, whereby the cell aggregates 61 were classified.

Figure 9:
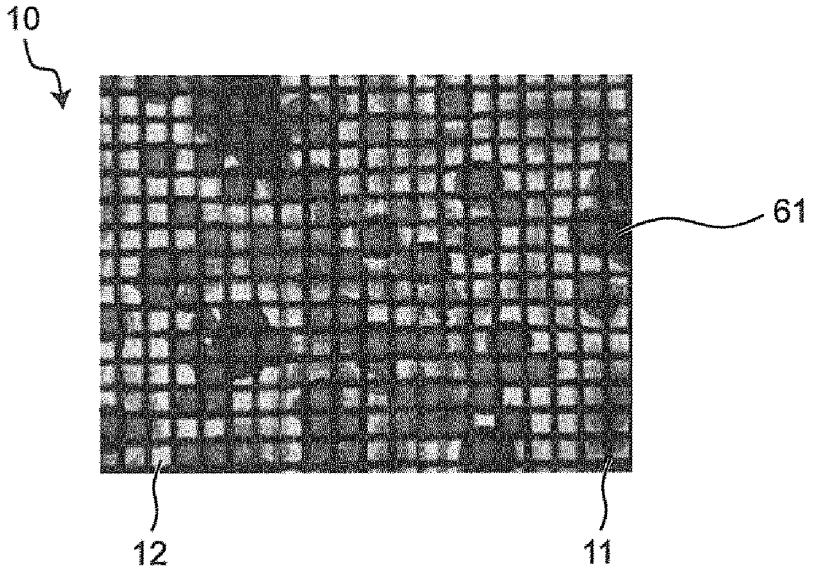
FIG. 9 is a photograph obtained by image-capturing part of a metallic porous membrane having captured cell aggregates in an enlarged manner in a first working example.
Figure 10:
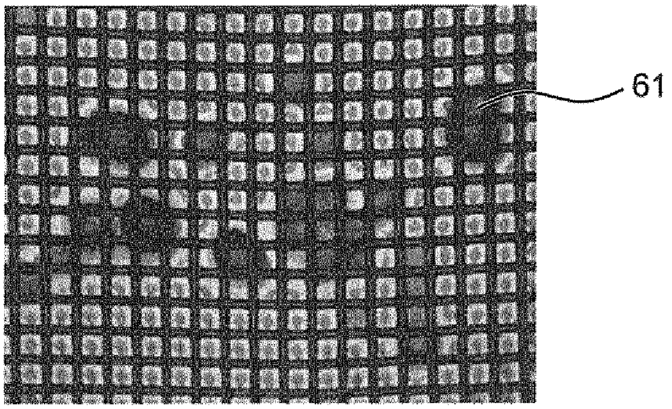
FIG. 10 is a photograph obtained by image-capturing part of a nylon mesh having captured cell aggregates in an enlarged manner in a first comparative example.

FIG. 9 shows part of a photograph of the metallic porous membrane 10 after having classified the cell aggregates 61 in the first working example. FIG. 10 shows part of a photograph of the nylon mesh after having classified the cell aggregates 61 in the first comparative example.

It can be understood that the metallic porous membrane 10 of the first working example shown in FIG. 9 has captured more cell aggregates 61 in number than the nylon mesh of the first comparative example shown in FIG. 10. That is, it can be understood that more cell aggregates 61 in number have been collected in the first working example than the first comparative example.

In a mesh structure of the first comparative example, when pressure is applied to the membrane section by the liquid 60 passing through, the through-holes are deformed. As such, there is a case in which the cell aggregate 61 larger in size than the through-hole of the nylon mesh undesirably passes through the deformed through-hole. Because of this, in the first comparative example, it can be thought of that the cell aggregates 61 with a dimension to be collected could not be collected by the nylon mesh.

Figure 11:
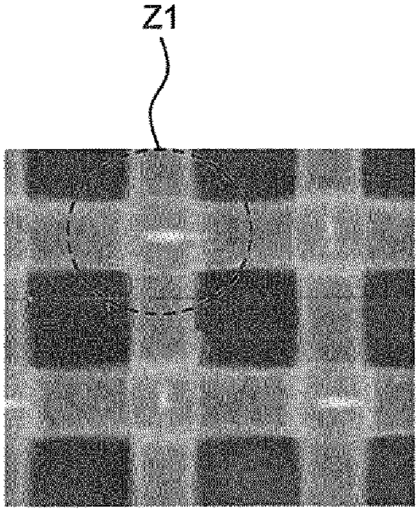
FIG. 11 is a photograph obtained by image-capturing an intersecting portion of the nylon mesh of the first comparative example in an enlarged manner.

FIG. 11 shows an enlarged photograph of an intersecting portion Z1 of the nylon mesh. Because the nylon mesh is produced by interweaving linear nylon, a stepped portion is formed in a thickness direction of the nylon mesh at the intersecting portion Z1 where pieces of linear nylon intersect with each other. In other words, a principal surface of the nylon mesh for capturing the cell aggregates 61 becomes a surface undesirably including uneven portions due to a plurality of stepped portions. Because of this, there is a case in which the cell aggregate 61 capable of passing through the through-hole of the nylon mesh is undesirably caught by the intersecting portion Z1. The cell aggregate 61 caught by the intersecting portion Z1 of the nylon mesh as described above cannot be collected in some case. Even if the cell aggregate 61 caught by the intersecting portion Z1 of the nylon mesh is collected, the collected cell aggregate 61 does not have a desired dimension. Accordingly, the cell aggregate 61 to be originally classified cannot be obtained.

In contrast, in the metallic porous membrane 10 of the first working example, the through-hole 12 is unlikely to be deformed even if the pressure is applied to the membrane section 11 by the liquid 60 passing through. Because of this, the cell aggregate 61 larger than the through-hole 12 of the metallic porous membrane 10 is unlikely to pass through the through-hole 12. Further, the first principal surface PS1 of the metallic porous membrane 10 is formed to be flat in the first working example. As such, in the first working example, the cell aggregate 61 with a dimension capable of passing through the through-hole 12 can pass through the through-hole 12 without being caught in the first principal surface PS1 of the metallic porous membrane 10. Accordingly, it can be thought of that more cell aggregates 61 were able to be collected in the first working example than the first comparative example. Further, it can be thought of that the cell aggregates 61 with an enhanced dimension accuracy can be collected in the first working example compared to the first comparative example.

As discussed above, with the nylon mesh of the first comparative example, a reduction in the collection rate of the cell aggregates 61, an error in the classification, and a reduction in reproductivity are generated. Accordingly, with the metallic porous membrane 10 of the first working example, the collection rate of the cell aggregates 61, the classification accuracy, and the reproductivity can be enhanced in comparison with the nylon mesh.

(Second Working Example)

In a second working example, the plurality of cell aggregates 61*a*, 61*b*, and 61*c* having different dimensions were classified using the classifying device 50 of the first embodiment. As for the dimensions of the cell aggregates 61*a*, 61*b*, and 61*c*, the dimension of the cell aggregate 61*a* is largest while the dimension of the cell aggregate 61*c* is smallest.

In the second working example, the classifying device 50 of the first embodiment was used. The metallic porous membranes 10A, 10B, and 10C of the classifying device 50 are circular meshes made of nickel. The outer diameter of each of the metallic porous membranes 10A, 10B, and 10C is 7.8 mm, and the membrane sections 11*a*, 11*b*, and 11*c* each having a diameter of 6 mm are formed in the center portion. In the membrane sections 11*a*, 11*b*, and 11*c*, the square through-holes 12*a*, 12*b*, and 12*c* are respectively provided in the tetragonal lattice arrangement. The dimensions of the through-holes 12*a*, 12*b*, and 12*c* are as follows: that is, one sides of the respective squares are 180 μm, 120 μm, and 58 μm; lattice intervals are 260 μm, 170 μm, and 76.3 μm; and thicknesses are 20 μm, 17 μm, and 20 μm. The metallic porous membranes 10A, 10B, and 10C have experienced the sterilization process by gamma-irradiation before the classification is performed. In the classifying device 50 of the second working example, the metallic porous membranes 10A, 10B, and 10C are arranged in that order from an upstream side of a flow path of the liquid 60.

Figure 12:
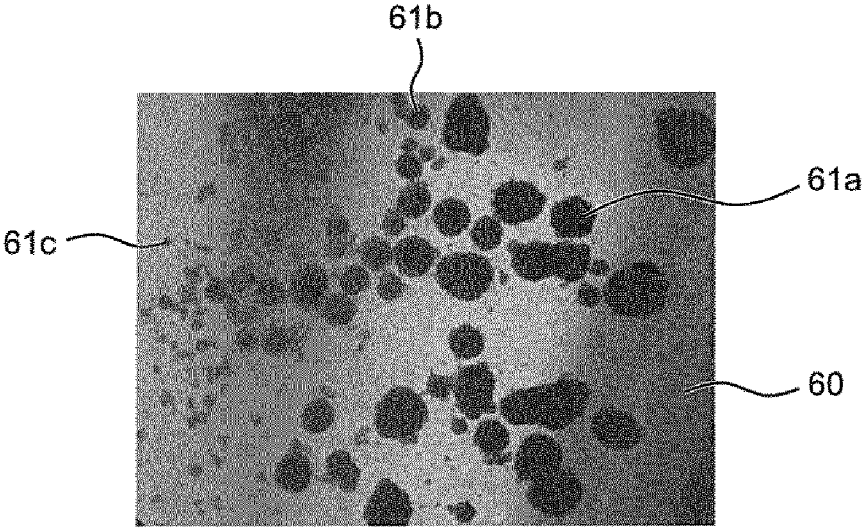
FIG. 12 is a photograph showing a liquid containing cell aggregates of different dimensions.

FIG. 12 shows the liquid 60 containing cell aggregates having different dimensions in the second working example. In the second working example, the liquid 60 of 1 ml containing the cell aggregates having different dimensions as shown in FIG. 12 was supplied into the classifying device 50 and filtered by a dead-end system, so as to classify the cell aggregates 61*a*, 61*b*, and 61*c*. The metallic porous membranes 10A, 10B, and 10C were taken out five minutes later after the start of filtering. Next, 5-ml physiological saline was made to pass through each of the metallic porous membranes 10A, 10B, and 10C from a surface not capturing the cell aggregates (second principal surface PS2) in a state in which a surface capturing the cell aggregates (first principal surface PS1) was made to face downward, whereby the cell aggregates were collected in a petri dish. The collected cell aggregates were observed under a microscope.

Figure 13:
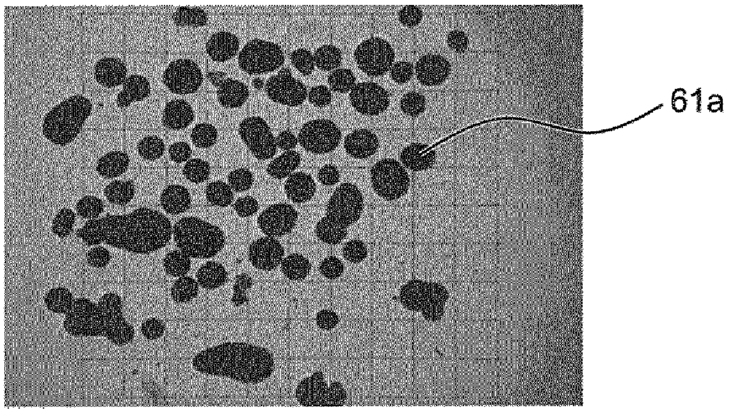
FIG. 13 is an enlarged photograph of cell aggregates collected by an uppermost metallic porous membrane in a second working example.

FIG. 13 shows an enlarged photograph of the cell aggregates collected by the metallic porous membrane 10A in the second working example. It can be understood that, as shown in FIG. 13, the cell aggregates 61*a* larger than the through-holes 12*a* are captured in the metallic porous membrane 10A.

Figure 14:
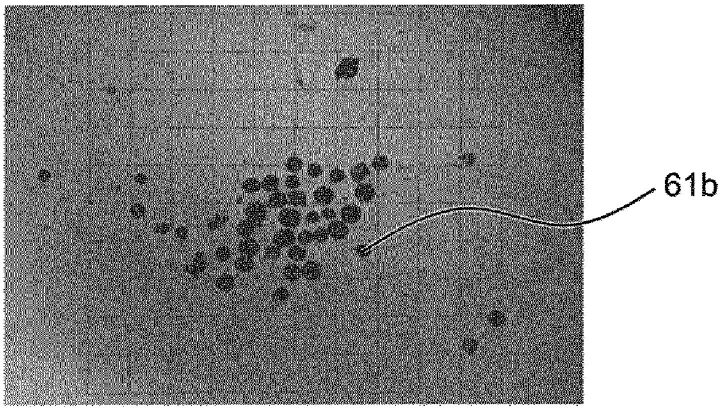
FIG. 14 is an enlarged photograph of cell aggregates collected by a center metallic porous membrane in the second working example.

FIG. 14 shows an enlarged photograph of the cell aggregates collected by the metallic porous membrane 10B in the second working example. It can be understood that, as shown in FIG. 14, the cell aggregates 61*b* larger than the through-holes 12*b* are captured in the metallic porous membrane 10B.

Figure 15:
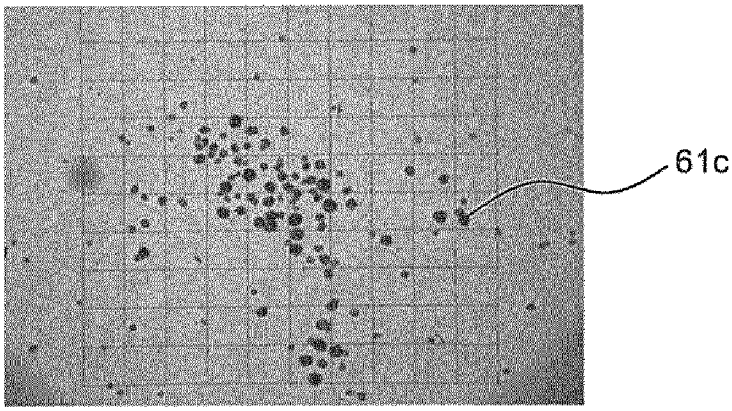
FIG. 15 is an enlarged photograph of cell aggregates collected by a lowermost metallic porous membrane in the second working example.

FIG. 15 shows an enlarged photograph of the cell aggregates collected by the metallic porous membrane 10C in the second working example. It can be understood that, as shown in FIG. 15, the cell aggregates 61*c* larger than the through-holes 12*c* are captured in the metallic porous membrane 10C.

In addition, the liquid 60 was filtered to be classified under the same conditions as those of the second working example described above, and then part of each of the liquids 60A, 60B, and 60C after having been filtered by the metallic porous membranes 10A, 10B, and 10C was observed under a microscope in an enlarged manner.

Figure 16:
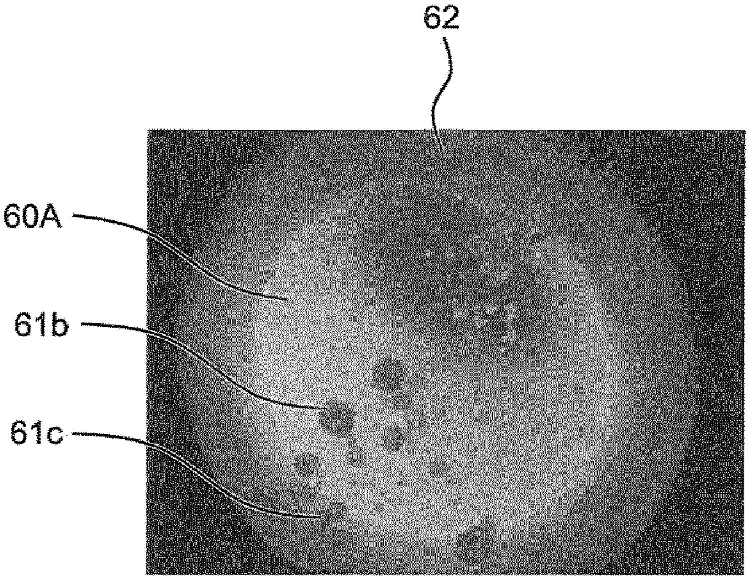
FIG. 16 is a photograph obtained by image-capturing part of a liquid after having passed through the uppermost metallic porous membrane in an enlarged manner in the second working example.

FIG. 16 shows a photograph in which part of the liquid 60A after having passed through the metallic porous membrane 10A is enlarged in the second working example. As shown in FIG. 16, it can be understood that the cell aggregates 61*b*, 61*c* and the isolated cell 62 are contained in the liquid 60A having passed through the metallic porous membrane 10A but the cell aggregate 61*a* is not contained therein.

Figure 17:
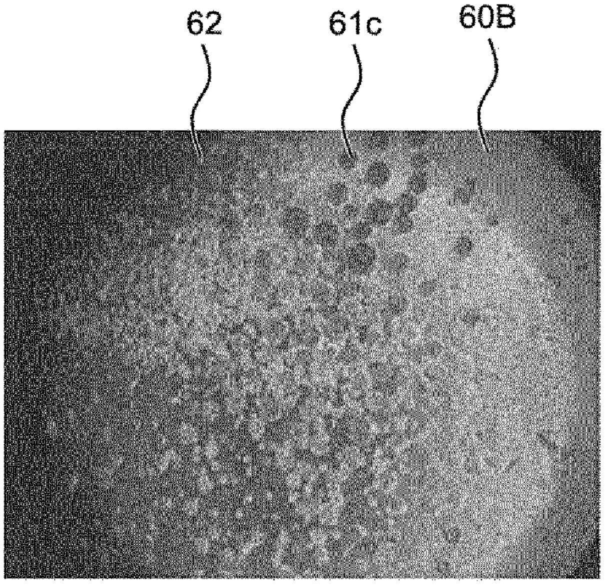
FIG. 17 is a photograph obtained by image-capturing part of a liquid after having passed through the center metallic porous membrane in an enlarged manner in the second working example.

FIG. 17 shows a photograph in which part of the liquid 60B after having passed through the metallic porous membrane 10B is enlarged in the second working example. As shown in FIG. 17, it can be understood that the cell aggregate 61*c* and the isolated cell 62 are contained in the liquid 60B having passed through the metallic porous membrane 10B but the cell aggregate 61*b* is not contained therein.

Figure 18:
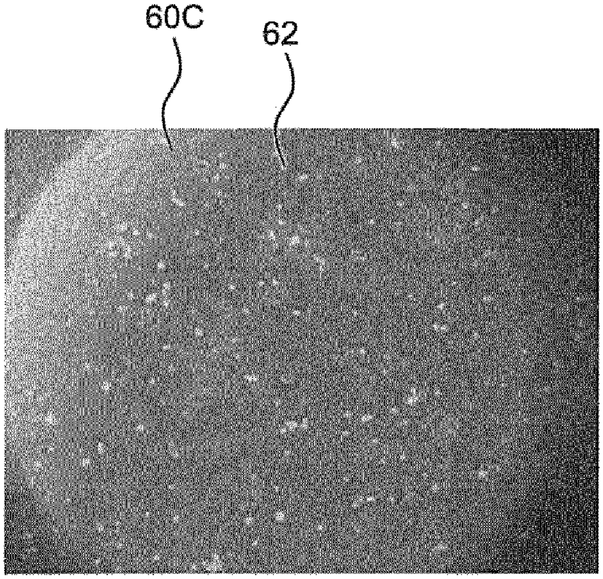
FIG. 18 is a photograph obtained by image-capturing part of a liquid after having passed through the lowermost metallic porous membrane in an enlarged manner in the second working example.

FIG. 18 shows a photograph in which part of the liquid 60C after having passed through the metallic porous membrane 10C is enlarged in the second working example. As shown in FIG. 18, it can be understood that the isolated cell 62 is contained in the liquid 60C having passed through the metallic porous membrane 10C but the cell aggregate 61*c* is not contained therein.

As discussed thus far, the classifying device 50 of the second working example can capture the cell aggregates 61*a*, 61*b*, and 61*c* of the desired dimensions in the metallic porous membranes 10A, 10B, and 10C, respectively. In other words, the classifying device 50 of the second working example can classify the cell aggregates 61*a*, 61*b*, and 61*c* having mutually different dimensions in the stepwise manner.

(Third Working Example)

In a third working example, cultured cell aggregates (spheroids) were classified in accordance with sizes of the cell aggregates using the classifying device 50 of the first embodiment.

The cell aggregates were cultured such that NIH3T3 cells in which ras genes had been introduced were cultured in a DMEM culture medium of 1% PCSM containing 10% FBS. A container used was a 3.5-mm dish, and the number of disseminated cells was $3\times10^5$/ml. The cells were cultured in an incubation at 37° C. for 24 hours, and as a result, cell aggregates of various sizes were able to be produced.

Figure 19:
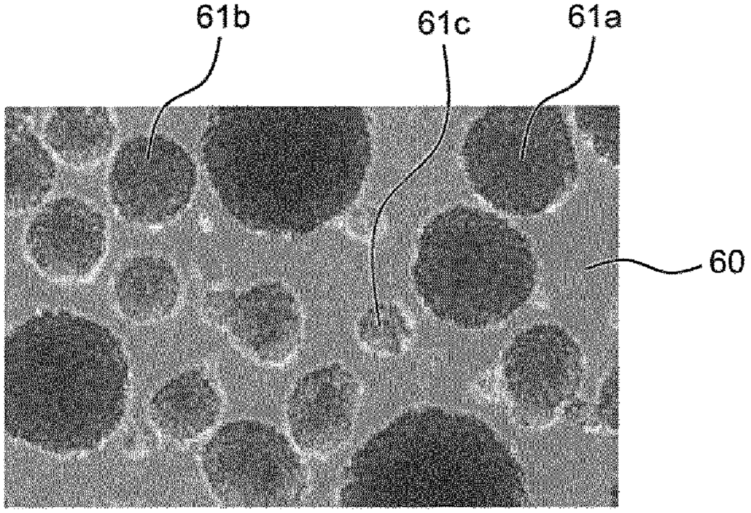
FIG. 19 is a photograph obtained by image-capturing part of cultured cell aggregates in an enlarged manner in a third working example.

FIG. 19 shows a photograph in which part of the cultured cell aggregates is enlarged. As shown in FIG. 19, it can be understood that the cell aggregates 61*a*, 61*b*, and 61*c* having mutually different sizes are produced before the classification.

In the third working example, the hole sizes of the through-holes 12*a*, 12*b*, and 12*c* of the metallic porous membranes 10A, 10B, and 10C in the classifying device 50 are 180 μm, 100 μm, and 58 μm, respectively. Here, the through-holes 12*a*, 12*b*, and 12*c* are each formed in a square shape, and the hole size refers to the length d of one side of the hole of the square shape.

In the third working example, the culture medium 60 containing the cell aggregates 61*a*, 61*b*, and 61*c* having mutually different sizes as shown in FIG. 19 was made to pass through the metallic porous membranes 10A, 10B, and 10C in that order, whereby the cell aggregates 61*a*, 61*b*, and 61*c* were classified. Specifically, three 3.5-mm dishes, in each of which a culture fluid was newly supplied, were prepared, and the cell aggregates 61*a*, 61*b*, and 61*c* captured by the metallic porous membranes 10A, 10B, and 10C were moved to the corresponding 3.5-mm dishes by being back-washed.

Figure 20:
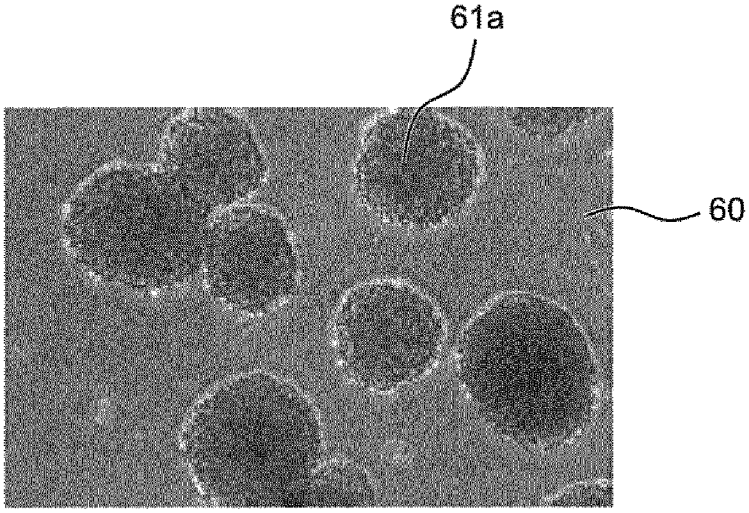
FIG. 20 is an enlarged photograph of cell aggregates captured by an uppermost metallic porous membrane in the third working example.
Figure 21:
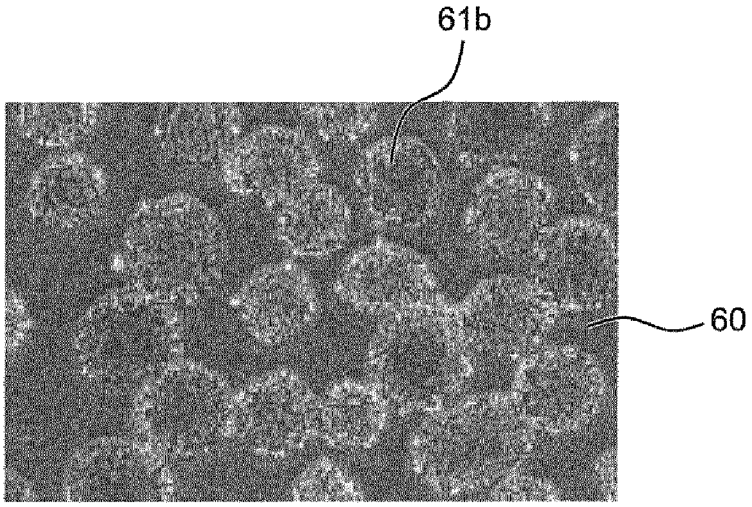
FIG. 21 is an enlarged photograph of cell aggregates captured by a center metallic porous membrane in the third working example.
Figure 22:
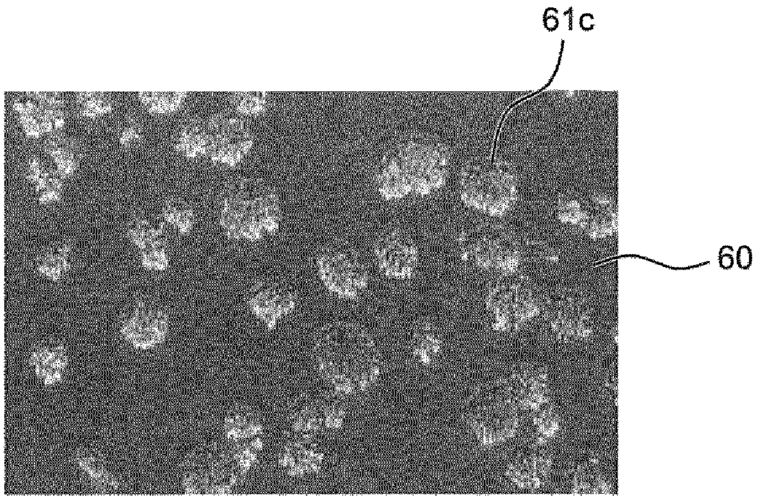
FIG. 22 is an enlarged photograph of cell aggregates captured by a lowermost metallic porous membrane in the third working example.
Figure 23:
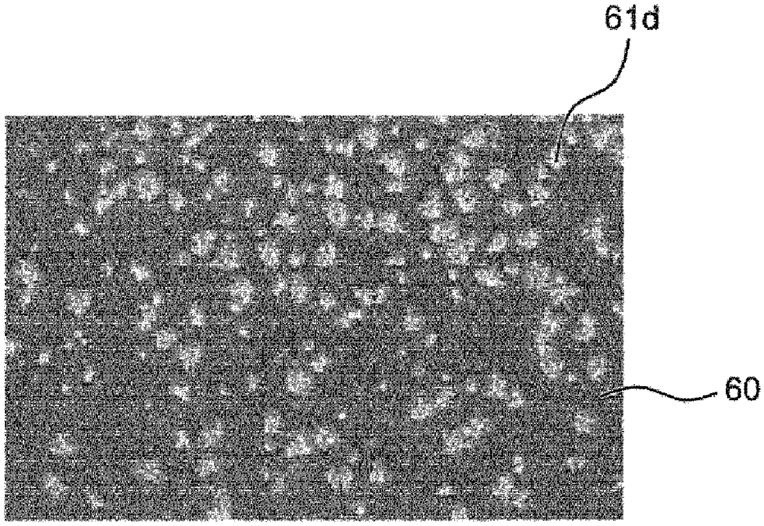
FIG. 23 is a photograph obtained by image-capturing part of a liquid after having passed through the lowermost metallic porous membrane in an enlarged manner in the third working example.

FIG. 20 shows a photograph in which part of the cell aggregate 61*a* captured by the metallic porous membrane 10A is enlarged in the third working example. FIG. 21 shows a photograph in which part of the cell aggregate 61*b* captured by the metallic porous membrane 10B is enlarged in the third working example. FIG. 22 shows a photograph in which part of the cell aggregate 61*c* captured by the metallic porous membrane 10C is enlarged in the third working example. FIG. 23 shows a photograph in which part of the liquid 60 after having passed through the metallic porous membrane 10C is enlarged in the third working example.

It can be understood that, as shown in FIGS. 20 to 22, the cell aggregates 61*a*, 61*b*, and 61*c* respectively having substantially equal sizes are captured in the metallic porous membranes 10A, 10B, and 10C. Further, as shown in FIG. 23, it can be understood that the cell aggregates 61*a*, 61*b*, and 61*c* are not contained in the liquid 60 having passed through the metallic porous membrane 10C but a cell aggregate 61*d* smaller in size than the cell aggregates 61*a*, 61*b*, and 61*c* is contained therein. The liquid 60 after having passed the metallic porous membrane 10C may contain, for example, the isolated cell 62 or the like in addition to the cell aggregate 61*d*.

In the third working example, as discussed above, the following can be understood: that is, the culture medium 60 containing the cell aggregates 61*a*, 61*b*, and 61*c* having mutually different sizes (see FIG. 19) was made to pass through the metallic porous membranes 10A, 10B, and 10C, whereby the cell aggregates 61*a*, 61*b*, and 61*c* were able to be classified in accordance with their sizes (see FIGS. 20 to 23).

Next, in order to examine a relationship between size and activity of cell aggregates, the culture medium containing the cell aggregates was equally divided for each dish, and ATP active mass was measured with respect to one culture medium of the equally divided medium. In this case, the ATP active mass was measured using an ATP quantifying assay (CellTiter-Glo (registered trademark), Promega). The ATP active mass refers to activity of a cell, that is, the probability of survival of a cell. In other words, it means that, as the value of the ATP active mass is larger, the number of living cells is larger. The other culture medium of the equally divided medium was used for re-culture which will be explained later.

The cell aggregates in the dishes were selected one by one at random with a pipette and supplied into a U-bottom plate (375-well). Then, the diameter and the ATP active mass of each cell aggregate were measured using Cell Imager. Selected were 17 cell aggregates 61*a* from among the cell aggregates 61*a* captured by the metallic porous membrane 10A with the hole size being 180 μm, 20 cell aggregates 61*b* from among the cell aggregates 61*b* captured by the metallic porous membrane 10B with the hole size being 100 μm, and 12 cell aggregates 61*c* from among the cell aggregates 61*c* captured by the metallic porous membrane 10C with the hole size being 58 μm.

Figure 24:
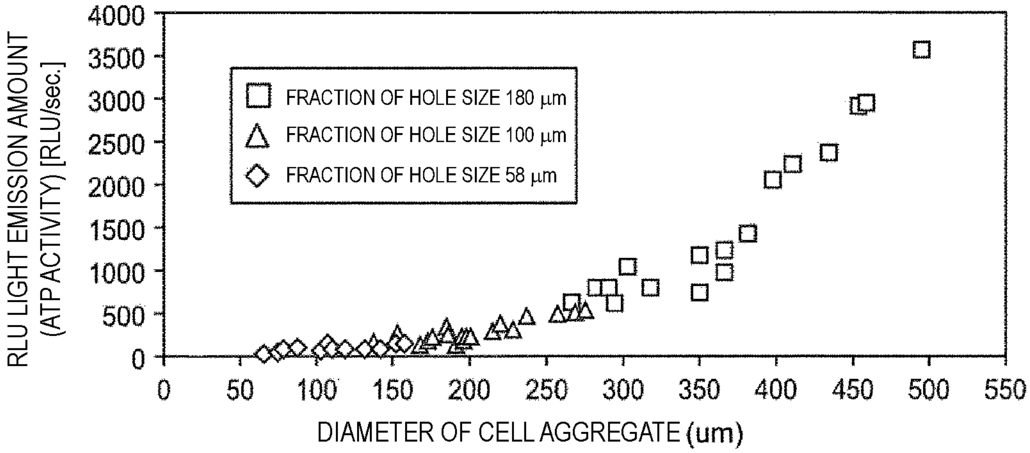
FIG. 24 is a graph showing a measurement result of ATP active mass with respect to a diameter of a cell aggregate in the third working example.

FIG. 24 is a graph showing a measurement result of the ATP active mass with respect to the diameter of a cell aggregate in the third working example. The horizontal axis in FIG. 24 represents the diameter of a cell aggregate, and the vertical axis represents the ATP active mass. In FIG. 24, square points show the data related to the cell aggregates 61*a* captured by the metallic porous membrane 10A with the hole size being 180 μm, triangular points show the data related to the cell aggregates 61*b* captured by the metallic porous membrane 10B with the hole size being 100 μm, and rhombic points show the data related to the cell aggregates 61*c* captured by the metallic porous membrane 10C with the hole size being 58 μm.

It can be understood that, as shown in FIG. 24, the activity of the cells captured by the respective metallic porous membranes 10A, 10B, and 10C is maintained. To be specific, the ATP active mass is such that the value of the active mass (RLU light emission amount) is larger as the number of living cells is larger. The cell aggregate is configured to include a larger number of cells as the size of the cell aggregate becomes larger. Because of this, as the size of the cell aggregate is larger, the value of the ATP active mass becomes larger if the cells included in the cell aggregate are alive.

As shown in FIG. 24, it can be understood that the value of the ATP active mass becomes larger as the diameter of the cell aggregate becomes larger. From this, it can be understood that the activity of the cells captured by the respective metallic porous membranes 10A, 10B, and 10C is maintained. That is, it can be understood that the cells captured by the respective metallic porous membranes 10A, 10B, and 10C are alive. Originally, only the cells near a surface of the cell aggregate are maintained to be active while the cells at the center of the cell aggregate have lost their activity. Because of this, the relationship between the diameter and the ATP active mass of the cell aggregate exhibits a quadratic or cubic curve.

As for the cell aggregates captured by the respective metallic porous membranes 10A, 10B, and 10C, maximum values, minimum values, average values, and standard deviations of the diameters of the cell aggregates are shown in Table 1.

TABLE 1

| Diameter of Cell Aggregate | Fraction of Hole Size 180 μm (n = 17) | Fraction of Hole Size 100 μm (n = 20) | Fraction of Hole Size 58 μm (n = 12) |
|---|---|---|---|
| Maximum Value (μm) | 495 | 268 | 158 |
| Minimum Value (μm) | 267 | 138 | 65 |
| Average Value (μm) | 365 | 203 | 111 |
| Standard Deviation | 68 | 36 | 30 |

As shown in Table 1, the maximum values of the diameters of the cell aggregates captured by the metallic porous membrane 10A with the hole size being 180 μm, the metallic porous membrane 10B with the hole size being 100 μm, and the metallic porous membrane 10C with the hole size being 58 μm were respectively 495 μm, 268 μm, and 158 μm. The minimum values of the diameters of the captured cell aggregates were 267 μm, 138 μm, and 65 μm in the order of the metallic porous membranes 10A, 10B, and 10C. The average values of the diameters of the captured cell aggregates were 365 μm, 203 μm, and 111 μm in the order of the metallic porous membranes 10A, 10B, and 10C. The standard deviations of the captured cell aggregates were 68, 36, and 30 in the order of the metallic porous membranes 10A, 10B, and 10C. Ratios of the standard deviations to the corresponding average values of the captured cell aggregates were 19%, 18%, and 27% in the order of the metallic porous membranes 10A, 10B, and 10C.

Further, the cell aggregates 61*a*, 61*b*, and 61*c* having been classified were re-cultured. The other culture medium of the equally divided medium described above was used for the re-culture.

Figure 25:
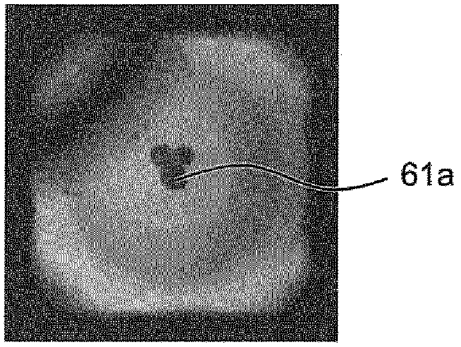
FIG. 25 is a photograph of a group of cell aggregates captured by a metallic porous membrane with a hole size being 180 μm in the third working example.
Figure 26:
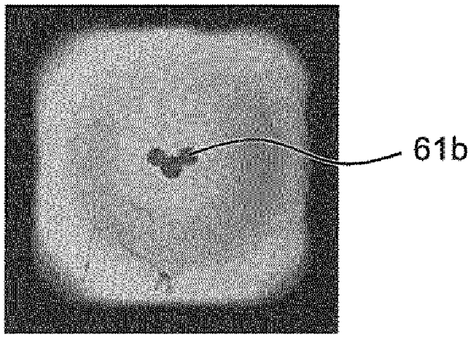
FIG. 26 is a photograph of a group of cell aggregates captured by a metallic porous membrane with a hole size being 100 μm in the third working example.
Figure 27:
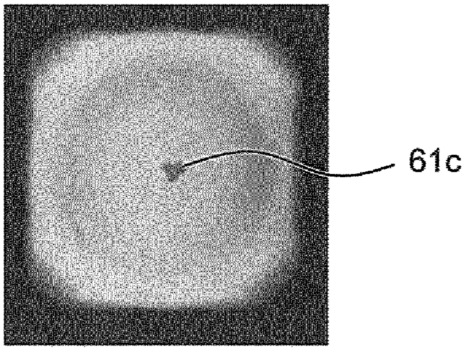
FIG. 27 is a photograph of a group of cell aggregates captured by a metallic porous membrane with a hole size being 58 μm in the third working example.

Of the cell aggregates 61*a*, 61*b*, and 61*c* in the dishes, three cell aggregates each were selected at random as one group with a pipette, and the one group was supplied into a U-bottom plate (375-well). FIG. 25 shows a photograph of a group of the cell aggregates 61*a* captured by the metallic porous membrane 10A with the hole size being 180 μm in the third working example. FIG. 26 shows a photograph of a group of the cell aggregates 61*b* captured by the metallic porous membrane 10B with the hole size being 100 μm in the third working example. FIG. 27 shows a photograph of a group of the cell aggregates 61*c* captured by the metallic porous membrane 10C with the hole size being 58 μm in the third working example.

In the third working example, produced were 33 groups of the cell aggregates 61*a*, as shown in FIG. 25, captured by the metallic porous membrane 10A, 43 groups of the cell aggregates 61*b*, as shown in FIG. 26, captured by the metallic porous membrane 10B with the hole size being 100 μm, and 34 groups of the cell aggregates 61*c*, as shown in FIG. 27, captured by the metallic porous membrane 10C with the hole size being 58 μm. These were cultured in the incubation at 37° C. for 24 hours, and as a result, one cell aggregate was able to be produced from three cell aggregates.

Figure 28:
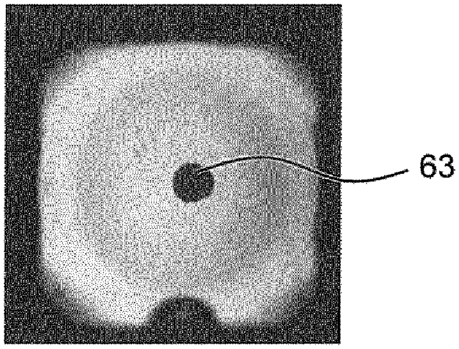
FIG. 28 is a photograph of a cell aggregate produced by culturing three cell aggregates shown in FIG. 25 captured by the uppermost metallic porous membrane in the third working example.
Figure 29:
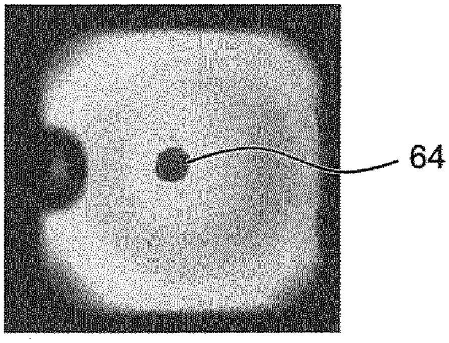
FIG. 29 is a photograph of a cell aggregate produced by culturing three cell aggregates shown in FIG. 26 captured by the center metallic porous membrane in the third working example.
Figure 30:
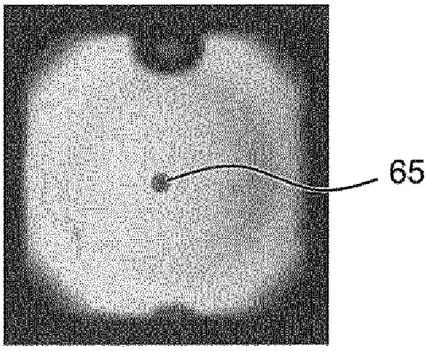
FIG. 30 is a photograph of a cell aggregate produced by culturing three cell aggregates shown in FIG. 27 captured by the lowermost metallic porous membrane in the third working example.

FIG. 28 shows a photograph of one cell aggregate 63 produced by culturing three cell aggregates 61*a*, as shown in FIG. 25, having been captured by the metallic porous membrane 10A in the third working example. FIG. 29 shows a photograph of one cell aggregate 64 produced by culturing three cell aggregates 61*b*, as shown in FIG. 26, having been captured by the metallic porous membrane 10B. FIG. 30 shows a photograph of one cell aggregate 65 produced by culturing three cell aggregates 61*c*, as shown in FIG. 27, having been captured by the metallic porous membrane 10C.

Sizes of the cell aggregates 63, 64, and 65 shown in FIGS. 28 to 30, having been produced by re-culturing, were measured using the above-mentioned Cell Imager. Average values and standard deviations of the sizes of the cell aggregates 63, 64, and 65 were respectively 340±81 μm, 194±34 μm, and 110±30 μm. Ratios of the standard deviations to the corresponding average values of the sizes of the cell aggregates 63, 64, and 65 were respectively 24%, 18%, and 27%. These values were equivalent to those in Table 1, which shows the result of the classification using the metallic porous membranes 10A, 10B, and 10C.

The above results indicate that, in the production of cell aggregates, cell aggregates of desired sizes can be classified from a culture medium, which contains cell aggregates having different sizes, by using the metallic porous membranes 10A, 10B, and 10C. The above results also indicate that, in the case where culturing is further performed on the cell aggregates classified using the metallic porous membranes 10A, 10B, and 10C, sizes of the cultured cell aggregates are likely to be uniformed.

(Fourth Working Example)

In a fourth working example, medicine efficacy research was carried out using the cell aggregates (spheroids) classified using the classifying device 50 of the first embodiment. In addition, as a second comparative example, medicine efficacy research was carried out using the cell aggregates that had not experienced the classification, that is, using the cell aggregates having different sizes.

In the fourth working example and the second comparative example, medicine efficacy of an anticancer drug Bortezomib was researched. Bortezomib is a proteasome inhibitor used to treat recurrence or intractable multiple myeloma. It is well-known that, as a mechanism of action, Bortezomib brings antitumor action by apoptosis induction, inhibition of proliferation, and inhibition of angiogenesis. It is also well-known that Bortezomib inhibits activation of NF-kB, and brings adhesion inhibition and/or inhibition of IL-6 secretion.

The cell aggregates were cultured such that NIH3T3/EGFP cells in which ras genes had been introduced were cultured in a DMEM culture medium of 1% PCSM containing 10% FBS. A container used was a 3.5-mm dish, and the number of disseminated cells was $1\times10^5$/ ml. The cells were cultured in the incubation at 37° C. for 24 hours, and as a result, cell aggregates of various sizes were able to be produced. The culture medium containing the above cell aggregates was equally divided into two portions, and one of them was used in the fourth working example while the other of them was used in the second comparative example.

In the fourth working example, after having passed through the metallic porous membrane 10A with the hole size being 180 μm and the metallic porous membrane 10B with the hole size being 100 μm, the cell aggregates captured on the metallic porous membrane 10B were selected one by one and supplied into a U-bottom plate (375-well). Then, the diameter and volume of each cell aggregate were measured with the Cell Imager.

In the fourth working example, Bortezomib was inputted into the wells in the amounts of 1, 3, 10, 20, and 100 nM, respectively. Then, after culturing for 24 hours in the incubation at 37° C., the ATP active mass was measured using the ATP quantifying assay (CellTiter-Glo (registered trademark), Promega). Then, after further culturing for 24 hours (48 hours in total) in the incubation at 37° C., the ATP active mass was measured.

Figure 31:
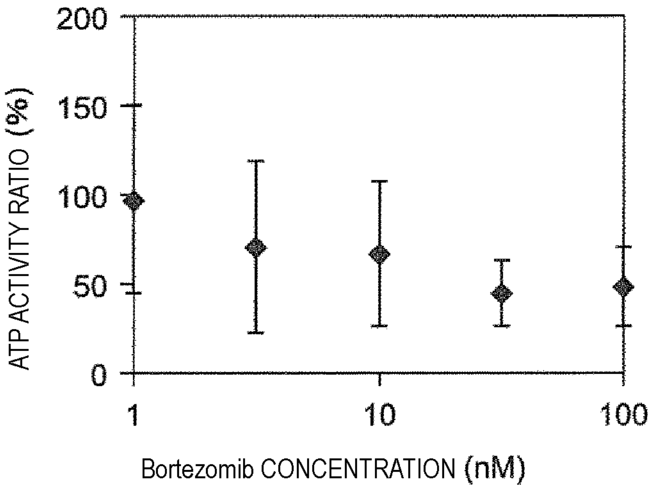
FIG. 31 is a graph showing a measurement result of ATP active mass of cell aggregates having been cultured for 24 hours after the input of Bortezomib in the amounts of 1, 3, 10, 20, and 100 nM, respectively, in a fourth working example.
Figure 32:
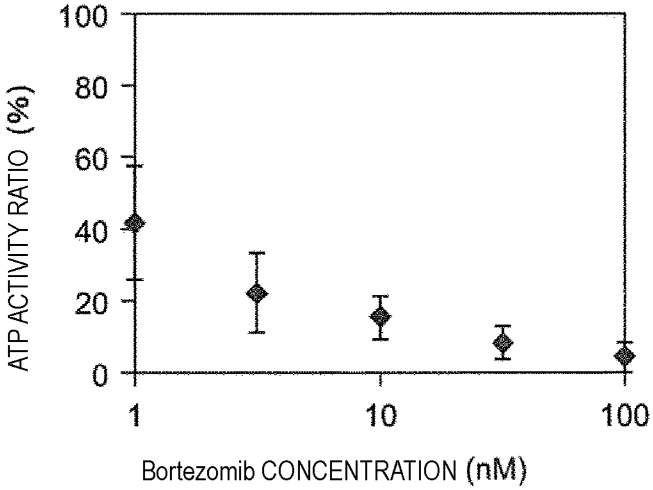
FIG. 32 is a graph showing a measurement result of ATP active mass of cell aggregates having been cultured for 48 hours after the input of Bortezomib in the amounts of 1, 3, 10, 20, and 100 nM, respectively, in the fourth working example.

FIG. 31 shows a measurement result of the ATP active mass of the cell aggregates having been cultured for 24 hours after the input of Bortezomib in the amounts of 1, 3, 10, 20, and 100 nM, respectively, in the fourth working example. FIG. 32 shows a measurement result of the ATP active mass of the cell aggregates having been cultured for 48 hours after the input of Bortezomib in the amounts of 1, 3, 10, 20, and 100 nM, respectively, in the fourth working example. In each of FIGS. 31 and 32, the vertical axis represents an ATP activity ratio, and the horizontal axis represents Bortezomib concentration.

In contrast, in the second comparative example, without performing classification using the metallic porous membrane, the cell aggregates were selected one by one and supplied into a U-bottom plate (375-well). Then, the diameter and the volume of each cell aggregate were measured with the Cell Imager.

In the second comparative example, Bortezomib was inputted into the wells in the amounts of 1, 3, 10, 20, and 100 nM, respectively. Then, after culturing for 24 hours in the incubation at 37° C., the ATP active mass was measured using the ATP quantifying assay (CellTiter-Glo (registered trademark), Promega). Then, after further culturing for 24 hours (48 hours in total) in the incubation at 37° C., the ATP active mass was measured.

Figure 33:
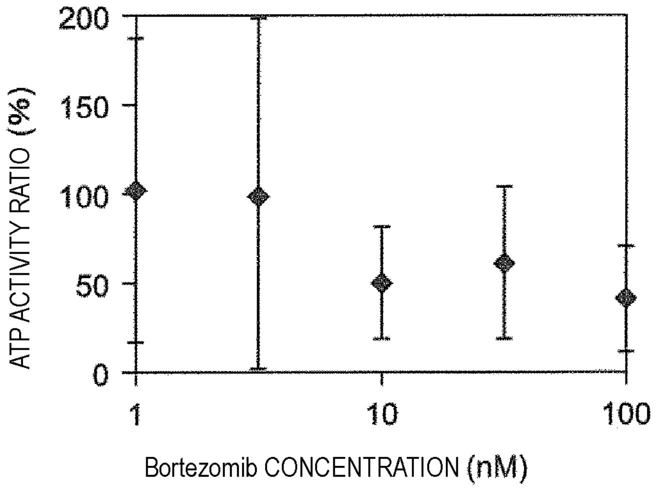
FIG. 33 is a graph showing a measurement result of ATP active mass of cell aggregates having been cultured for 24 hours after the input of Bortezomib in the amounts of 1, 3, 10, 20, and 100 nM, respectively, in a second comparative example.
Figure 34:
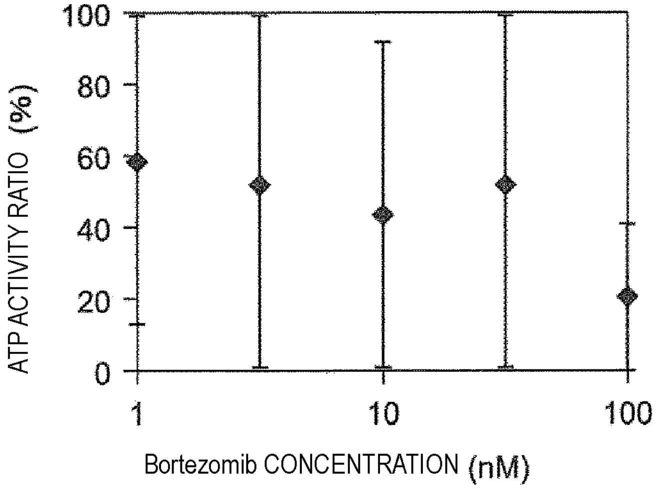
FIG. 34 is a graph showing a measurement result of ATP active mass of cell aggregates having been cultured for 48 hours after the input of Bortezomib in the amounts of 1, 3, 10, 20, and 100 nM, respectively, in the second comparative example.

FIG. 33 shows a measurement result of the ATP active mass of the cell aggregates having been cultured for 24 hours after the input of Bortezomib in the amounts of 1, 3, 10, 20, and 100 nM, respectively, in the second comparative example. FIG. 34 shows a measurement result of the ATP active mass of the cell aggregates having been cultured for 48 hours after the input of Bortezomib in the amounts of 1, 3, 10, 20, and 100 nM, respectively, in the second comparative example. In each of FIGS. 33 and 34, the vertical axis represents the ATP activity ratio, and the horizontal axis represents the Bortezomib concentration.

When the ATP activity ratios of the fourth working example shown in FIGS. 31 and 32 and the ATP activity ratios of the second comparative example shown in FIGS. 33 and 34 are compared with each other, it can be understood that error bars of the fourth working example are smaller than those of the second comparative example. This indicates that, in a medicine efficacy examination (medicine efficacy research or medicine efficacy development) using cell aggregates, a highly reliable result can be obtained by performing the medicine efficacy examination using the cell aggregates of uniform size obtained by classification using the metallic porous membrane 10. In other words, classifying the cell aggregates using the metallic porous membrane 10 brings an effect that a medicine efficacy examination result can be obtained with high accuracy. Because the metallic porous membrane 10 has a higher mechanical strength than a nylon mesh or the like, its classification accuracy is higher. Accordingly, with the metallic porous membrane 10, in a medicine efficacy examination, an error in the examination result due to the size of the cell aggregates can be made small in comparison with the nylon mesh or the like.

(Fifth Working Example)

In the fifth working example, in order to research influence of the metallic porous membrane 10 on the culture of cell aggregates, cell aggregates were cultured in a state in which the metallic porous membrane 10 having experienced flame sterilization was soaked in a culture fluid. In addition, as a third comparative example, cell aggregates were cultured in a state in which the metallic porous membrane 10 was not soaked in a culture fluid.

In the fifth working example and the third comparative example, NIH3T3 cells in which ras genes had been introduced were cultured in a culture medium where 5% FCS and 1% PCSM were added to a Dulbecco's Modified Eagle Medium DMEM (manufacture by Nacalai tesque).

Figure 35:
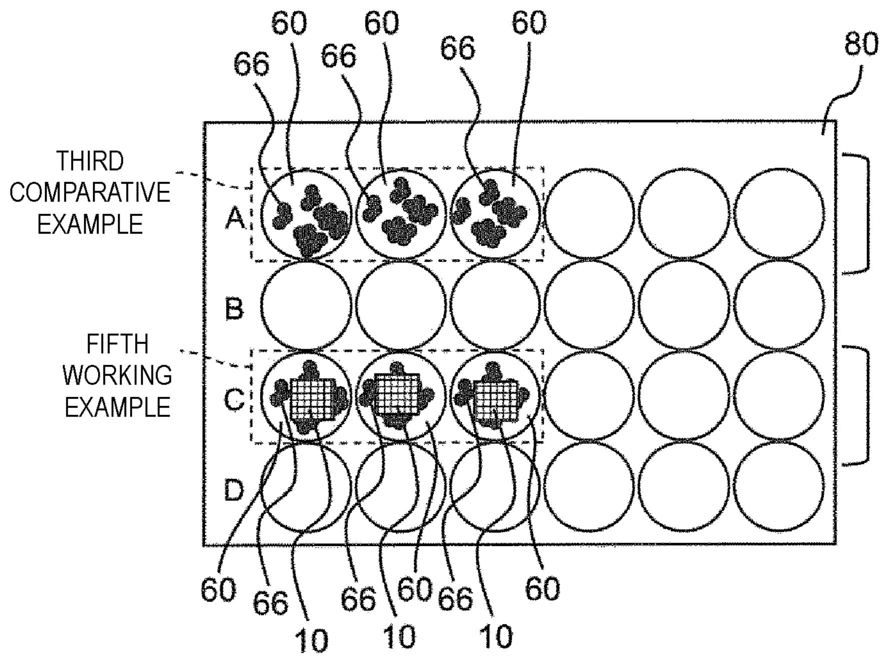
FIG. 35 is a diagram illustrating a culturing state of cells 66 in a fifth working example and a third comparative example.

FIG. 35 illustrates a culturing state of cells 66 in the fifth working example and the third comparative example. As shown in FIG. 35, a well plate 80 (Sumilon tight plate 24F manufactured by Sumitomo Bakelite) was prepared. In the well plate 80, the cells 66 and the culture medium 60 of the third comparative example were disseminated in three wells of an A row, while the cells 66 and the culture medium 60 of the fifth working example were disseminated in three wells of a C row. The amount of dissemination per well was such that the number of cells was $7.0\times10^4$, and the culture medium was 2 ml.

In the fifth working example, three metallic porous membranes 10 were prepared and exposed to a burner for one second. Thereafter, the metallic porous membranes 10 were cut and soaked in the culture media 60 in the wells. The outer diameter and the thickness of the metallic porous membrane 10 used in the fifth working example were 18 mm and 40 μm, respectively. The through-hole 12 was formed in a square shape, and the length of one side of the stated square shape was 58 μm. The distance b between two through-holes 12 was 18 μm.

In the fifth working example, the cells 66 were cultured for 10 minutes in a state in which the metallic porous membranes 10 were soaked in the culture media 60, and thereafter the metallic porous membranes 10 were removed. In contrast, in the third comparative example, the cells 66 were cultured for 10 minutes without the metallic porous membranes 10 being soaked in the culture media. Then, the active mass of the cells cultured in each of the fifth working example and the third comparative example was confirmed by a method as follows.

The culture media 60 and the cells 66 of the fifth working example as well as the culture media 60 and the cells 66 of the third comparative example were respectively divided into 20 portions so as to be dispensed to separate plates. An ATP reagent, manufactured by TOYOINK, was added in the amount of 100 μl to each of the dispensed portions of the culture media and the cells, and thereafter the RLU light emission amount (ATP active mass) was measured with a plate reader (Fusion α-FP manufactured by Perkin Elmer).

Figure 36:
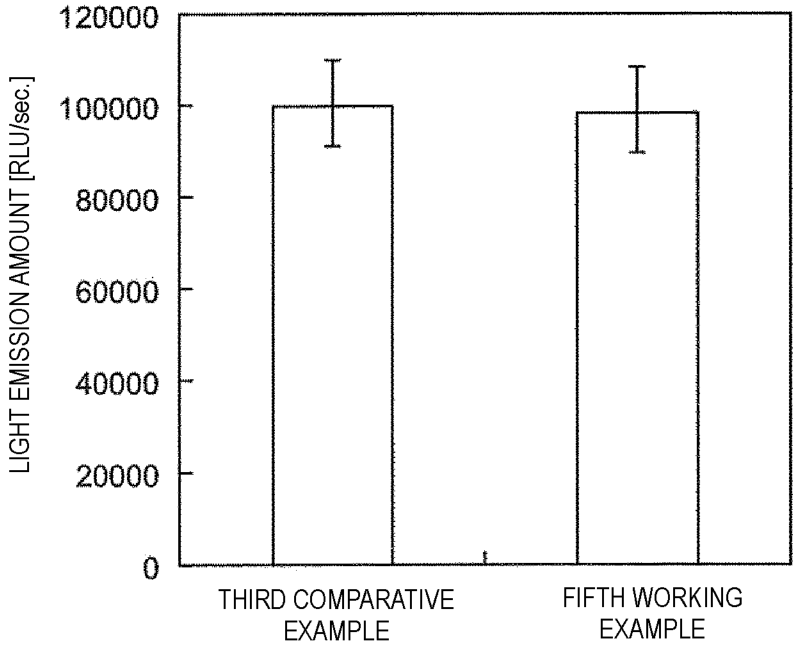
FIG. 36 is a graph showing a measurement result of an RLU light emission amount (ATP active mass) of cultured cells in the fifth working example and the third comparative example.

FIG. 36 shows a measurement result of the RLU light emission amount (ATP active mass) of the cultured cells in each of the fifth working example and the third comparative example. As shown in FIG. 36, it can be understood that the RLU light emission amount (ATP active mass) of the fifth working example is equivalent to that of the third comparative example when compared with each other. This indicates that the metallic porous membranes 10 having experienced the flame sterilization do not have any influence on the culture of the cells.

(Sixth Working Example)

In a sixth working example, cell aggregates (spheres or embryoid bodies) derived from cultured mouse ES cells were classified in accordance with their sizes using the classifying device 50 of the first embodiment. The metallic porous membrane 10 is a circular mesh made of nickel. The outer diameter of the metallic porous membrane 10 is 7.8 mm, and the membrane section 11 with a diameter of 6 mm is formed in the center portion of the metallic porous membrane 10. In the membrane section 11, the through-holes 12 formed in a square shape are provided in tetragonal lattice arrangement. One side of the through-hole 12 is 120 μm in length. An interval between the through-holes 12, that is, a distance of a metal portion between two through-holes 12 is 50 μm. To rephrase, a lattice interval between the through-holes 12 is 170 μm. The thickness is 17 μm. The metallic porous membrane 10 has experienced the sterilization process by gamma-irradiation before the classification is performed. In the sixth working example, the liquid 60 containing the cell aggregates 61 having different dimensions as shown in FIG. 37 was made to pass through the metallic porous membrane 10 to be filtered, whereby the cell aggregates 61 were classified.

The cell aggregates were cultured such that mouse ES cells were cultured in a DMEM culture medium of 1% PCSM containing 10% FBS. A container used was a 3.5-mm dish, and the number of disseminated cells was $3\times10^5$/ml. The cells were cultured in the incubation at 37° C. for 48 hours, and as a result, cell aggregates of various sizes were able to be produced.

Figure 37:
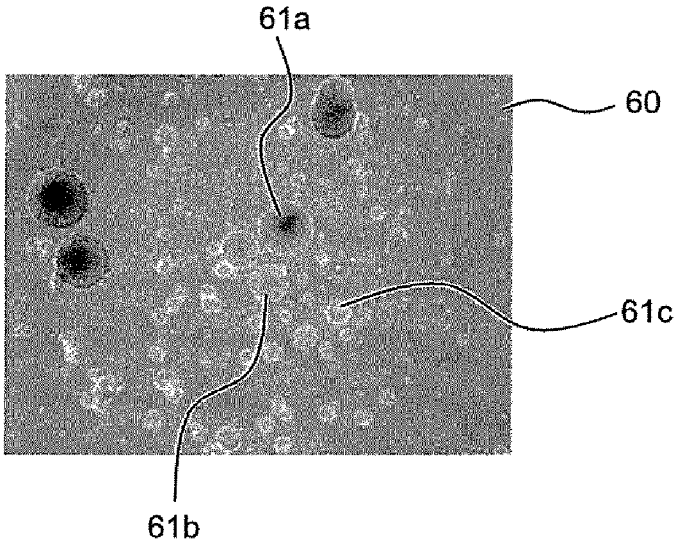
FIG. 37 is a photograph obtained by image-capturing part of cultured cell aggregates in an enlarged manner in a sixth working example.

FIG. 37 shows a photograph in which part of the cultured cell aggregates is enlarged. As shown in FIG. 37, it can be understood that the cell aggregates 61*a*, 61*b*, and 61*c* having mutually different sizes are produced before the classification.

In the sixth working example, the hole sizes of the through-holes 12*a*, 12*b*, and 12*c* of the metallic porous membranes 10A, 10B, and 10C in the classifying device 50 are 180 μm, 100 μm, and 58 μm, respectively. Here, the through-holes 12*a*, 12*b*, and 12*c* are each formed in a square shape, and the hole size refers to the length d of one side of the hole of the square shape.

In the sixth working example, the culture medium 60 containing the cell aggregates 61*a*, 61*b*, and 61*c* having mutually different sizes as shown in FIG. 37 was made to pass through the metallic porous membranes 10A, 10B, and 10C in that order, whereby the cell aggregates 61*a*, 61*b*, and 61*c* were classified. Specifically, three 3.5-mm dishes, in each of which a culture fluid was newly supplied, were prepared, and the cell aggregates 61*a*, 61*b*, and 61*c* captured by the metallic porous membranes 10A, 10B, and 10C were moved to the corresponding 3.5-mm dishes by being back-washed.

Figure 38:
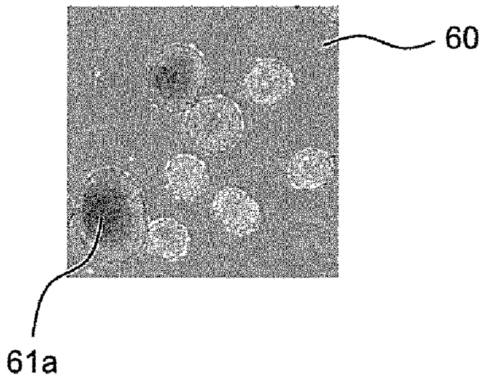
FIG. 38 is an enlarged photograph of cell aggregates captured by an uppermost metallic porous membrane in the sixth working example.
Figure 39:
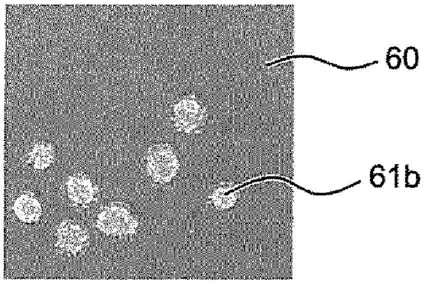
FIG. 39 is an enlarged photograph of cell aggregates captured by a center metallic porous membrane in the sixth working example.
Figure 40:
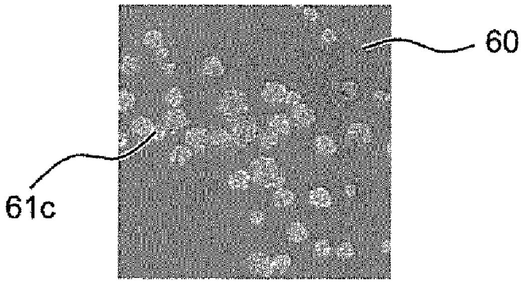
FIG. 40 is an enlarged photograph of cell aggregates captured by a lowermost metallic porous membrane in the sixth working example.
Figure 41:
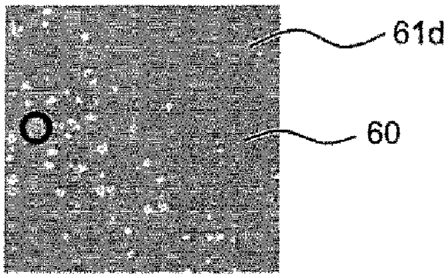
FIG. 41 is a photograph obtained by image-capturing part of a liquid after having passed through the lowermost metallic porous membrane in an enlarged manner in the sixth working example.

FIG. 38 shows a photograph in which part of the cell aggregate 61*a* captured by the metallic porous membrane 10A is enlarged in the sixth working example. FIG. 39 shows a photograph in which part of the cell aggregate 61*b* captured by the metallic porous membrane 10B is enlarged in the sixth working example. FIG. 40 shows a photograph in which part of the cell aggregate 61*c* captured by the metallic porous membrane 10C is enlarged in the sixth working example. FIG. 41 shows a photograph in which part of the liquid 60 after having passed through the metallic porous membrane 10C is enlarged in the sixth working example.

It can be understood that, as shown in FIGS. 38 to 41, the cell aggregates 61*a*, 61*b*, and 61*c* respectively having substantially equal sizes are captured in the metallic porous membranes 10A, 10B, and 10C. Further, as shown in FIG. 41, it can be understood that the cell aggregates 61*a*, 61*b*, and 61*c* are not contained in the liquid 60 after having passed through the metallic porous membrane 10C but the cell aggregate 61*d* smaller in size than the cell aggregates 61*a*, 61*b*, and 61*c* is contained therein. The liquid 60 after having passed the metallic porous membrane 10C may contain, for example, the isolated cell 62 or the like in addition to the cell aggregate 61*d*.

In the sixth working example, as discussed above, the following can be understood: that is, the culture medium 60 containing the cell aggregates 61*a*, 61*b*, and 61*c* having mutually different sizes (see FIG. 37) was made to pass through the metallic porous membranes 10A, 10B, and 10C, whereby the cell aggregates 61*a*, 61*b*, and 61*c* were able to be classified in accordance with their sizes (see FIGS. 38 to 41).

Next, in order to examine a relationship between size and activity of cell aggregates, a culture medium containing cell aggregates were equally divided for each dish, and the ATP active mass was measured with respect to one culture medium of the equally divided medium. In this case, the ATP active mass was measured using an ATP quantifying assay (CellTiter-Glo (registered trademark), Promega). The ATP active mass refers to activity of a cell, that is, the probability of survival of a cell. In other words, it means that, as the value of the ATP active mass is larger, the number of living cells is larger. The other culture medium of the equally divided medium was used for re-culture which will be explained later.

The cell aggregates in the dishes were selected one by one at random with a pipette and supplied into a U-bottom plate (375-well). Then, the diameter and the ATP active mass of each cell aggregate were measured with the Cell Imager. Selected were 13 cell aggregates 61*a* from among the cell aggregates 61*a* captured by the metallic porous membrane 10A with the hole size being 180 μm, 10 cell aggregates 61*b* from among the cell aggregates 61*b* captured by the metallic porous membrane 10B with the hole size being 100 μm, and 16 cell aggregates 61*c* from among the cell aggregates 61*c* captured by the metallic porous membrane 10C with the hole size being 58 μm.

Figure 42:
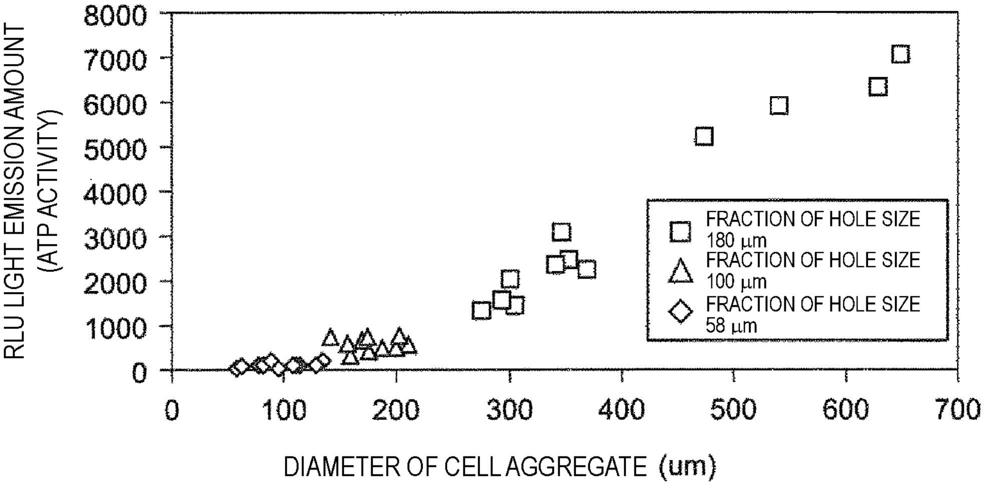
FIG. 42 is a graph showing a measurement result of ATP active mass with respect to a diameter of a cell aggregate in the sixth working example.

FIG. 42 shows a measurement result of the ATP active mass with respect to the diameter of a cell aggregate in the sixth working example. The horizontal axis in FIG. 42 represents the diameter of a cell aggregate, and the vertical axis represents the ATP active mass. In FIG. 42, square points show the data related to the cell aggregates 61*a* captured by the metallic porous membrane 10A with the hole size being 180 μm, triangular points show the data related to the cell aggregates 61*b* captured by the metallic porous membrane 10B with the hole size being 100 μm, and rhombic points show the data related to the cell aggregates 61*c* captured by the metallic porous membrane 10C with the hole size being 58 μm.

It can be understood that, as shown in FIG. 42, the activity of the cells captured by the respective metallic porous membranes 10A, 10B, and 10C is maintained. To be specific, the value of the ATP active mass (RLU light emission amount) is larger as the number of living cells is larger. The cell aggregate is configured to include a larger number of cells as the size of the cell aggregate becomes larger. Because of this, as the size of the cell aggregate is larger, the value of the ATP active mass becomes larger if the cells included in the cell aggregate are alive.

As shown in FIG. 42, it can be understood that the value of the ATP active mass becomes larger as the diameter of the cell aggregate becomes larger. From this, it can be understood that the activity of the cells captured by the respective metallic porous membranes 10A, 10B, and 10C is maintained. That is, it can be understood that the cells captured by the respective metallic porous membranes 10A, 10B, and 10C are alive. Originally, only the cells near a surface of the cell aggregate are maintained to be active while the cells at the center of the cell aggregate have lost their activity. Because of this, the relationship between the diameter and the ATP active mass of the cell aggregate exhibits a quadratic or cubic curve.

As for the cell aggregates captured by the respective metallic porous membranes 10A, 10B, and 10C, maximum values, minimum values, average values, and standard deviations of the diameters of the cell aggregates are shown in Table 2.

TABLE 2

| Diameter of Cell Aggregate | Fraction of Hole Size 180 μm (n = 13) | Fraction of Hole Size 100 μm (n = 10) | Fraction of Hole Size 58 μm (n = 16) |
|---|---|---|---|
| Maximum Value (μm) | 649 | 211 | 136 |
| Minimum Value (μm) | 276 | 142 | 59 |
| Average Value (μm) | 413 | 178 | 99 |
| Standard Deviation | 130 | 22 | 25 |

As shown in Table 2, the maximum values of the diameters of the cell aggregates captured by the metallic porous membrane 10A with the hole size being 180 μm, the metallic porous membrane 10B with the hole size being 100 μm, and the metallic porous membrane 10C with the hole size being 58 μm were respectively 649 μm, 211 μm, and 136 μm. The minimum values of the diameters of the captured cell aggregates were 276 μm, 142 μm, and 59 μm in the order of the metallic porous membranes 10A, 10B, and 10C. The average values of the diameters of the captured cell aggregates were 413 μm, 178 μm, and 99 μm in the order of the metallic porous membranes 10A, 10B, and 10C. The standard deviations of the captured cell aggregates were 68, 36, and 30 in the order of the metallic porous membranes 10A, 10B, and 10C. Ratios of the standard deviations to the corresponding average values of the captured cell aggregates were 31%, 12%, and 23% in the order of the metallic porous membranes 10A, 10B, and 10C.

Further, the cell aggregates 61*a*, 61*b*, and 61*c* having been classified were re-cultured. The other culture medium of the equally divided medium discussed above was used for the re-culture.

Figure 43:
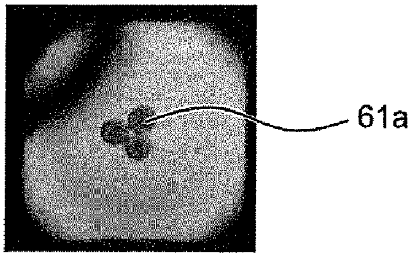
FIG. 43 is a photograph of a group of cell aggregates captured by a metallic porous membrane with a hole size being 180 μm in the sixth working example.
Figure 44:
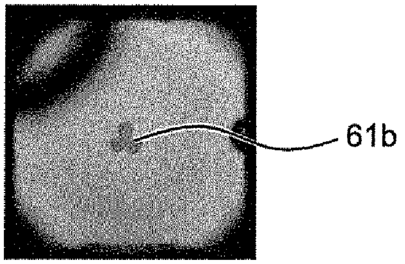
FIG. 44 is a photograph of a group of cell aggregates captured by a metallic porous membrane with a hole size being 100 μm in the sixth working example.
Figure 45:
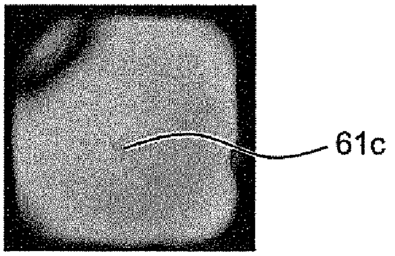
FIG. 45 is a photograph of a group of cell aggregates captured by a metallic porous membrane with a hole size being 58 μm in the sixth working example.

Of the cell aggregates 61*a*, 61*b*, and 61*c* in the dishes, three cell aggregates each were selected at random as one group with a pipette, and the one group was supplied into a U-bottom plate (375-well). FIG. 43 shows a photograph of a group of the cell aggregates 61*a* captured by the metallic porous membrane 10A with the hole size being 180 μm in the sixth working example. FIG. 44 shows a photograph of a group of the cell aggregates 61*b* captured by the metallic porous membrane 10B with the hole size being 100 μm in the sixth working example. FIG. 45 shows a photograph of a group of the cell aggregates 61*c* captured by the metallic porous membrane 10C with the hole size being 58 μm in the sixth working example.

In the sixth working example, produced were 30 groups of the cell aggregates 61*a*, as shown in FIG. 43, captured by the metallic porous membrane 10A, 17 groups of the cell aggregates 61*b*, as shown in FIG. 44, captured by the metallic porous membrane 10B with the hole size being 100 μm, and 50 groups of the cell aggregates 61*c*, as shown in FIG. 45, captured by the metallic porous membrane 10C with the hole size being 58 μm. These were cultured in the incubation at 37° C. for 24 hours, and as a result, one cell aggregate was able to be produced from three cell aggregates.

Figure 46:
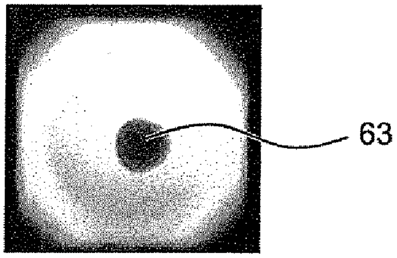
FIG. 46 is a photograph of a cell aggregate produced by culturing three cell aggregates shown in FIG. 43 captured by the uppermost metallic porous membrane in the sixth working example.
Figure 47:
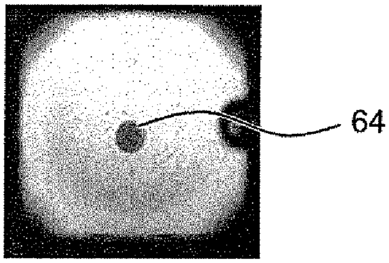
FIG. 47 is a photograph of a cell aggregate produced by culturing three cell aggregates shown in FIG. 44 captured by the center metallic porous membrane in the sixth working example.
Figure 48:
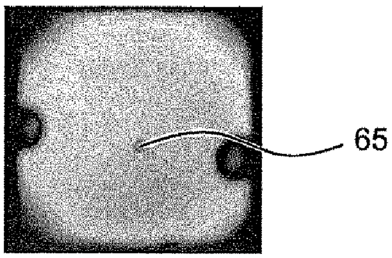
FIG. 48 is a photograph of a cell aggregate produced by culturing three cell aggregates shown in FIG. 45 captured by the lowermost metallic porous membrane in the sixth working example.

FIG. 46 shows a photograph of one cell aggregate 63 produced by culturing three cell aggregates 61*a*, as shown in FIG. 43, having been captured by the metallic porous membrane 10A in the sixth working example. FIG. 47 shows a photograph of one cell aggregate 64 produced by culturing three cell aggregates 61*b*, as shown in FIG. 44, having been captured by the metallic porous membrane 10B. FIG. 48 shows a photograph of one cell aggregate 65 produced by culturing three cell aggregates 61*c*, as shown in FIG. 45, having been captured by the metallic porous membrane 10C.

Sizes of the cell aggregates 63, 64, and 65 as shown in FIGS. 46 to 48, having been produced by re-culturing, were measured using the above-mentioned Cell Imager. Average values and standard deviations of the sizes of the cell aggregates 63, 64, and 65 were respectively 441±146 μm, 203±26 μm, and 114±34 μm. Ratios of the standard deviations to the corresponding average values of the sizes of the cell aggregates 63, 64, and 65 were respectively 33%, 13%, and 30%. These values were equivalent to those in Table 2, which shows the result of the classification using the metallic porous membranes 10A, 10B, and 10C.

The above results indicate that, in the production of cell aggregates, cell aggregates of desired sizes can be classified from a culture medium containing cell aggregates of different sizes by using the metallic porous membranes 10A, 10B, and 10C. The above results also indicate that, in the case where culturing is further performed on the cell aggregates classified using the metallic porous membranes 10A, 10B, and 10C, sizes of the cultured cell aggregates are likely to be uniformed.

The present invention is sufficiently described being related to preferred embodiments with reference to the accompanying drawings, and it is apparent to those skilled in the art that various variations and modifications can be carried out. Such variations and modifications should be taken to be included in the scope of the present invention without departing from the scope of the present invention as set out in the appended claims.

Because the present invention can classify cell aggregates while enhancing the collection rate of the cell aggregates, the invention is useful, for example, in the fields of medicine efficacy research, regenerative medical drug production, and so on.

REFERENCE SIGNS LIST

10, 10A, 10B, 10C METALLIC POROUS MEMBRANE
11, 11*a*, 11*b*, 11*c* MEMBRANE SECTION
12, 12*a*, 12*b*, 12*c* THROUGH-HOLE
20 HOUSING
21 FIRST HOUSING SECTION
21*a* FLUID INTRODUCING PATH
21*b* FLANGE SECTION
21*c* THROUGH-HOLE
21*d* TERMINAL END PORTION
22 SECOND HOUSING SECTION
22*a* FLUID DISCHARGING PATH
22*b* FLANGE SECTION
22*c* PROJECTION
22*d* TERMINAL END PORTION
50 CLASSIFYING DEVICE
60, 60A, 60B, 60C LIQUID
61, 61*a*, 61*b*, 61*c*, 61*d* CELL AGGREGATE
62 ISOLATED CELL
63, 64, 65 CELL AGGREGATE
66 CELL
70 DIRECTION IN WHICH LIQUID FLOWS
80 WELL PLATE
PS1 FIRST PRINCIPAL SURFACE
PS2 SECOND PRINCIPAL SURFACE

The invention claimed is:

1. A classifying device that classifies aggregates, the classifying device comprising:
- a plurality of metallic porous membranes respectively including:
  - a membrane section including a first principal surface for capturing the aggregates,
  - a second principal surface opposing the first principal surface, and
  - a plurality of through-holes communicating with the first principal surface and the second principal surface,
- wherein
- among each of the plurality of metallic porous membranes, the through-holes have mutually different dimensions, an opening ratio of a first area of the plurality of through-holes at the first principal surface to a projected entire area of the first principal surface is no less than 10%, and
- some of the plurality of through-holes in at least a first of the plurality of metallic porous membranes are configured to have different dimensions sufficient to release pressure applied to the first of the plurality of metallic porous membranes without degrading classification accuracy of the first of the plurality of metallic porous membranes,
- the plurality of metallic porous membranes are arranged in series from an upstream side of a flow path through which a liquid containing the aggregates flows in a descending order of the different dimensions of the through-holes of the plurality of metallic porous membranes.

2. The classifying device according to claim 1, wherein the dimension of the through-holes of a metallic porous membrane positioned at a lowermost stage among the plurality of metallic porous membranes, is equal to or smaller than a size of an aggregate to be isolated from the liquid.

3. The classifying device according to claim 1, wherein the dimension of the through-holes of a metallic porous membrane positioned at a lowermost stage among the plurality of metallic porous membranes have a size that allows an aggregate to be isolated from the liquid to pass through.

4. The classifying device according to claim 1, further comprising:
- a housing that encompasses the plurality of metallic porous membranes and includes a fluid introducing path that opposes the first principal surface of the plurality of metallic porous membranes and a fluid discharging path that opposes the second principal surface of the plurality of metallic porous membranes.

5. The classifying device according to claim 1, wherein the flow path in which a liquid containing the aggregates flows while passing through the plurality of metallic porous membrane is shut off from outside air.

6. The classifying device according to claim 1, wherein the plurality of metallic porous membranes are sterilized.

7. The classifying device according to claim 1, wherein the aggregates are cells.

* * * * *